US007583367B2

(12) United States Patent
Ikeda et al.

(10) Patent No.: US 7,583,367 B2
(45) Date of Patent: Sep. 1, 2009

(54) CATHETER SURGERY SIMULATION

(75) Inventors: Seiichi Ikeda, Nagoya (JP); Toshio Fukuda, Nagoya (JP); Ikuo Takahashi, Hekinan (JP)

(73) Assignee: National University Corporation Nagoya University, Aichi (JP)

( * ) Notice: Subject to any disclaimer, the term of this patent is extended or adjusted under 35 U.S.C. 154(b) by 148 days.

(21) Appl. No.: 11/913,301

(22) PCT Filed: May 2, 2006

(86) PCT No.: PCT/JP2006/309175

§ 371 (c)(1), (2), (4) Date: Oct. 31, 2007

(87) PCT Pub. No.: WO2006/120982

PCT Pub. Date: Nov. 16, 2006

(65) Prior Publication Data

US 2009/0015818 A1 Jan. 15, 2009

(30) Foreign Application Priority Data

| | | | |
|---|---|---|---|
| May 6, 2005 | (JP) | ............................. | 2005-134730 |
| Jun. 7, 2005 | (JP) | ............................. | 2005-167421 |
| Oct. 31, 2005 | (JP) | ............................. | 2005-315832 |
| Oct. 31, 2005 | (JP) | ............................. | 2005-315893 |
| Oct. 31, 2005 | (JP) | ............................. | 2005-315894 |

(51) Int. Cl.
*G01B 11/16* (2006.01)
*G01J 4/00* (2006.01)

(52) U.S. Cl. ............................ 356/32; 356/33; 356/364

(58) Field of Classification Search ............. 356/32–35, 356/364–369
See application file for complete search history.

(56) References Cited

U.S. PATENT DOCUMENTS

2005/0099600 A1 * 5/2005 Frey et al. ................... 351/205

FOREIGN PATENT DOCUMENTS

JP 1536395 6/2005

OTHER PUBLICATIONS

Fukuda, Toshio et al., "An In-Vitro Medical Model of the Human Cerebral Arteries for Trial Operations," Proceeding of the 20th Robot Academic Study, 2002).

Ikeda, Seiichi et al., "Phantom Based Training System for Intravascular Neurosurgery," Lecture Proceeding of Robotics and Mechatronics, 2003).

Ikeda, S. et al., "An In-Vitro Lithe Model of Individual Cerebral Artery for Neurosurgical Simulation," Proceeding of the 12gh Japan Society of Computer Aided Surgery, 2003).

* cited by examiner

*Primary Examiner*—Michael P Stafira
(74) *Attorney, Agent, or Firm*—Quarles & Brady LLP; Gavin J. Milczarek-Desai

(57) ABSTRACT

It is possible to observe a state of stress applied to a region around a cavity replicating a body cavity such as a blood vessel and the like in a three-dimensional model. In catheter insert simulation, when stress is applied to the region around the cavity in the three-dimensional model, it is possible to observe the catheter state together with a photoelastic effect corresponding to the stress state in the surrounding region caused by the catheter.

25 Claims, 21 Drawing Sheets

CATHETER SURGERY SIMULATION

TECHNICAL FIELD

The present invention relates to a catheter surgery simulator.

BACKGROUND ART

The present inventors have proposed a block-shaped three-dimensional model replicating a body cavity such as a blood vessel and the like of a subject (see patent document 1 and non-patent document 1). This three-dimensional model is obtained by laminate shaping a body cavity model such as a blood vessel and the like based on tomogram data of a subject, surrounding the circumference of the body cavity model by a molding material of a three-dimensional model, hardening the molding material of the three-dimensional model, and then removing the body cavity model.

By employing an elastomer material such as silicone rubber and the like as the molding material of the three-dimensional model, it is possible to observe a dynamic deformation of a cavity (a product replicating the blood vessel and the like) when liquid is sent or a catheter is inserted into the cavity.

Furthermore, the present inventors have proposed a membranous three-dimensional model (see, non-patent document 2).

Furthermore, the present inventors have proposed a three-dimensional model configured by using a gel-like base material (see, non-patent document 3).

[Patent document 1] International Publication No. WO 03/096308

[Non patent document 1] "Medical model for operation, which replicates the cavity of the cerebral blood vessel" (Proceeding of the 20th Robot Academic Study, 2002)

[Non patent document 2] "Study on operation simulator based on living body information subjecting to an operation of the neuroendovascular surgery." (Lecture Proceeding of robotics and mechatronics, 2003)

[Non patent document 3] "Surgery simulation three-dimensional model replicating the cerebrovascular cavity." (Proceeding of the 12th Japan Society of Computer Aided Surgery, 2003)

DISCLOSURE OF THE INVENTION

[Problems to be Solved by the Invention]

According to the above-mentioned models, it is possible to observe a dynamic deformation of a cavity portion replicating the body cavity by visual observation with respect to an insertion simulation of a catheter or liquid. However, no information about a state of stress applied to the region around the cavity portion can be obtained.

Therefore, an object of the present invention is to allow a state of stress applied to a region around a cavity portion in a three-dimensional model to be observed.

[Means to Solve the Problems]

The present invention addresses the problem discussed above, and has the following configuration.

A catheter surgery simulator that is a stress observation system of a three-dimensional model for detecting a photoelastic effect generated in light passing through a translucent three-dimensional model in which at least a region around a cavity replicating the body cavity is formed of an elastic material and into which a catheter can be inserted, including:

a polarized light source and its corresponding polarizing filter; and a phase shift filter disposed at the inner side of the polarized light source and its corresponding polarizing filter, wherein the catheter inserted in the three-dimensional model is made to be visible.

EFFECT OF THE INVENTION

According to thus configured stress observation system of a three-dimensional model, when a stress is applied to a region around the cavity of the three-dimensional model by an insertion simulation of a catheter or liquid, a photoelastic effect is generated and its state of stress can be observed.

For example, when a phase shift filter is disposed between a first polarizing filter constituting a polarized light source and a second polarizing filter at the side of an observer, a part of light that has passed through the first polarizing filter can pass through the second polarizing filter. At this time, when a catheter is inserted in the three-dimensional model, since the catheter does not transmit light, the catheter is observed as a shadow. Needless to say, in the region around a three-dimensional model in which a stress is changed by the catheter, a photoelastic effect can be observed. Note here that unless this phase shift filter is present, light from the light source is completely blocked by a pair of polarizing filters. Only light modulated by the photoelastic effect can pass through the second polarizing filter and can be observed. In this case, the catheter itself cannot be observed.

As the wavelength shift filter, a so-called one-wavelength plate or two-wavelength plate is preferably used. The one-wavelength plate is also referred to as a sensitive color plate and increases the observation sensitivity of the photoelastic effect.

REFERENCE MARKS IN THE DRAWINGS

Figure 1:
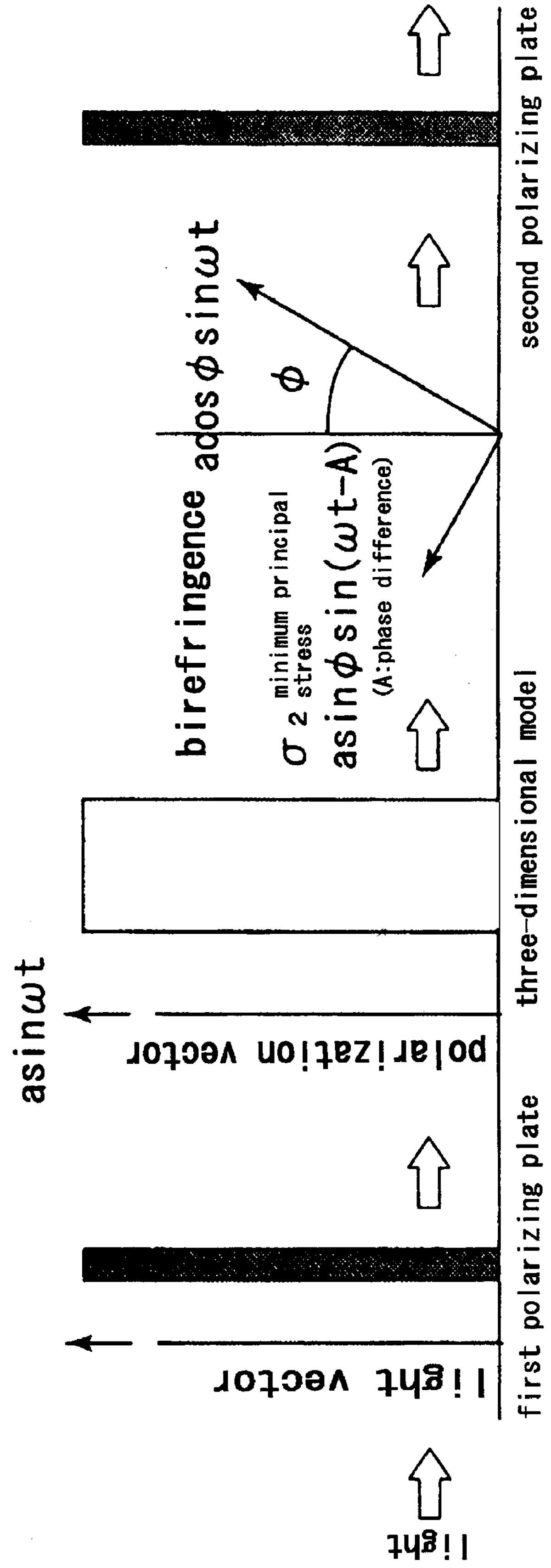
FIG. 1 is a view to illustrate a photoelastic effect.

11 core
12 body cavity model
15, 55 silicone rubber layer (membranous model)
21 three-dimensional model
22 base material
60, 80, 160, 300 catheter surgery simulator
61 light source
62, 63 polarizing plate
68 one-wavelength plate
70 photo-receiving portion
82, 83 ¼ wavelength plate

BEST MODE OF CARRYING OUT THE INVENTION

Hereinafter, each element of the present invention will be described in detail.

(Three-Dimensional Model Formation Material)

In order to observe a state of stress of a three-dimensional model by photoelasticity, in the three-dimensional model, a site that is required to be observed of at least the state of stress is formed of an isotropic material. The three-dimensional model has a light-transmittance property.

An example of materials having such a photoelasticity includes, in addition to elastomer such as silicone rubber (silicone elastomer) and thermosetting polyurethane elastomer, and the like, thermosetting resin such as silicone resin, epoxy resin, polyurethane, unsaturated polyester, phenol resin, urea resin, and the like, and thermoplastic resin such as polymethyl methacrylate and the like can be used alone or in combination thereof.

When a catheter or liquid is inserted into the cavity of the three-dimensional model, in order to allow the state of stress in the region around the cavity as a photoelastic effect to be observed, it is necessary that at least the region around the cavity is formed of an elastically deformable material. Needless to say, an entire three-dimensional model can be formed of an elastically deformable material.

As a formation material of such a three-dimensional model, a material that can be easily deformed in accordance with the insertion of a catheter and the like (that is, modulus of longitudinal elasticity is large) and that allows the change of the large photoelastic effect to be observed even in a slight deformation (that is, modulus of photoelasticity is large) is preferred. Such materials can include gelatin (animal-based agar). Furthermore, a gelling agent of polysaccharide, for example, vegetable agar, carrageenan, Locust bean gum, and the like, can be employed.

(Method of Forming Three-Dimensional Model)

In a three-dimensional model, a cavity can be made by replicating a body cavity such as a blood vessel and the like based on tomogram data of a subject.

Herein, a subject may be entire or a part of a human body, but an animal or a plant may be a target of tomography. Furthermore, it does not mean that dead bodies are excluded.

The tomogram data refer to basic data in carrying out the laminate shaping. In general, three-dimensional shape data are constructed from tomographic data obtained by an X-ray CT scanner, an MRI device, an ultrasonic device, and the like, and the three-dimensional shape data are resolved into two-dimensional data to obtain tomogram data.

Hereinafter, one example of generating tomogram data will be described.

Herein, a case where a plurality of two-dimensional images photographed in equal intervals while moving in parallel to the body axis direction are used as input data (tomographic data) is described, however, three-dimensional shape data of cavities can be also obtained by carrying out the same processing even in a case where two-dimensional images or three-dimensional images obtained by other photographing methods are used as input images. Firstly, each of the input two-dimensional images is exactly laminated based on the image-taking intervals at the time of tomography. Then, on each two-dimensional image, by specifying threshold values as to image intensity values, only targeting cavity regions of the body cavity model are extracted from each two-dimensional image, meanwhile other regions are removed from the laminated two-dimensional images. Thus, three-dimensional shapes of portions corresponding to cavity regions are provided as a shape in which two-dimensional images are laminated. The contours of these two-dimensional images are interpolated three-dimensionally to be reconstructed as a three-dimensional curved surface. Thereby, three-dimensional shape data of the targeted cavities are generated. Note here that in this case, by specifying the threshold value as to the intensity value, firstly the regions of cavities are extracted from the input image. However, besides this method, by specifying the specific intensity value giving the surfaces of the cavities, the surfaces of the cavities are extracted from the input image and interpolated three-dimensionally, whereby it is possible to generate three-dimensional curved surface directly. Furthermore, after extracting the regions by specifying the threshold value (or extracting the surfaces by specifying the specific intensity value), input images may be laminated. Furthermore, generation of a three-dimensional curved surface may be carried out by polygon approximation.

Note here that the three-dimensional shape data may be modified or altered during or after generation of the three-dimensional shape data. Examples of shape modification or alteration may include adding any structures that do not exist in tomographic data, adding a supporting structure called a support, removing a part of the structures in the tomographic data, altering shapes of cavities, or the like. Thereby, it is possible to modify or change the shapes of cavities formed inside the three-dimensional model freely. Furthermore, it is also possible to provide a non-rapid prototyped region inside of the cavities. As mentioned below, in a case of producing a body cavity model in which the inside presents a hollow structure and a non-rapid prototyped region is provided, three-dimensional shape data in which such a non-rapid prototyped region is provided in the cavities are generated. Note here that such processing may be carried out by a laminate shaping system or software that corresponds to the laminate shaping system.

Next, the generated three-dimensional shape data of cavities are converted into a format that corresponds to the laminate shaping system to be used for laminate shaping of the body cavity model if necessary, and sent to the laminate shaping system or the software that corresponds to the laminate shaping system to be used.

In the laminate shaping system (or the software that corresponds to the laminate shaping system), at the same time of setting various kinds of items such as arrangement or laminating direction of the body cavity model at the time of laminate shaping, for the purpose of maintaining the shape during the laminate shaping, supports (supporting structures) are added to portions that need supports (it is not necessary to add them unless necessary). Finally, by slicing thus obtained shaped data based on the shaped thickness at the time of laminate shaping, sliced data (tomogram data) directly used for laminate shaping are generated. Note here that on the contrary to the above-mentioned procedure, supports may be added after generating slice data. Furthermore, when sliced data are automatically generated by a laminate shaping system to be used (or software that corresponds to the laminate shaping system), this procedure may be omitted. However, also in this case, setting of the thickness of laminate shaping may be carried out. The same is true to the addition of supports, and when the support is automatically generated by the laminate shaping system (or software that corresponds to the laminate shaping system), the sliced data need not to be generated manually (may be generated manually).

In the above-mentioned examples, three-dimensional shape data are constructed from tomographic data. However, also in a case where three-dimensional shape data are given as data from the first, by resolving the three-dimensional shape data into two-dimensional data and thus tomogram data to be used in the following laminate shaping step may be obtained.

The present invention targets the body cavity such as blood vessels and the like. The body cavity herein refers to body cavities existing in various organs (skeletons, muscles, circulatory organs, respiratory organs, digestive organs, urogenital organs, endocrine organs, nerves, sense organs, etc.), as well as body cavities configured by geometry of various organs or body walls. Therefore, cavity of organs such as heart cavity, gastric cavity, intestinal cavity, uterine cavity, blood vessel lumen, urinary tract lumen, etc. and oral cavity, nasal cavity, fauces, middle ear cavity, body cavity, articular cavity, pericardial cavity, etc. are included in "body cavity."

From the above-mentioned tomogram data, the above-mentioned body cavity model will be formed.

The forming method is not particularly limited, but laminate shaping is preferable. Rapid prototyping herein denotes obtaining a predetermined shape by forming a thin layer based on tomogram data and repeating it sequentially.

The rapid prototyped body cavity model must be decomposed and removed in the following process. In order to facilitate removing, it is preferable that materials used for laminate shaping are materials with a low melting point or materials that are easily dissolved in a solvent. As such materials, thermosetting resin with a low melting point, or wax, and the like may be used. In addition, light-curing resin generally used in a so-called light-curing method (included in laminate shaping) can be used if easily decomposed.

The body cavity model can be made thin, in which the inside thereof has a hollow structure as long as it has a strength that can be resistant to an external force such as pressure added from the outside when it is surrounded by the three-dimensional model molding material in the following process. Thus, it is possible not only to reduce time used for laminate shaping and the cost accompanied with shaping but also to simplify the elution of the body cavity model in the later elution step.

Examples of specific laminate shaping methods include a powder sintering method, a melted resin jet method, a resin extrusion method, etc.

Note here that to the body cavity model produced by laminate shaping, after laminate shaping, various workings (removing working and addition working) such as surface polishing or addition of surface coating can be added, thereby making it possible to modify or change the shape of the body cavity model. When a support necessary to be removed after laminate shaping is added, support is removed, as a part of such workings.

Coating the surface of the body cavity model with other materials makes it possible to prevent a part or entire components of the body cavity model material from diffusing into the molding materials of the three-dimensional model. In addition to the above, also by physically treating (thermal treatment, high frequency treatment, etc.) or chemically treating the surface of the body cavity model, such diffusion can be prevented.

It is preferable that by surface treating the body cavity model, the level difference on the surface is smoothed. This makes the surface of the lumen of the three-dimensional model to be smooth and can replicate the inner surface of the body cavity such as a blood vessel more realistically. Examples of the surface treating methods include bringing the surface of the body cavity model with a solvent, melting the surface by heating, coating, and the combination thereof.

A part or entire part of the body cavity model is surrounded by a molding material of the three-dimensional model, followed by hardening thereof. By removing the body cavity model, a three-dimensional model is formed.

(Other Three-Dimensional Model)

The three-dimensional model may be formed to have a multi-layer structure.

That is to say, a three-dimensional model is produced from a membranous model having a cavity replicating a body cavity such as a blood vessel and the like therein, and a base material surrounding the membranous model.

According to thus configured three-dimensional model, a membranous structure of the blood vessel of the living body and a structure including physical properties of the soft tissue around the blood vessel can be individually replicated. Thus, a state in which a model having a membranous structure such as a blood vessel, and the like, and having flexibility is embedded in a base material having elasticity of the tissues surrounding the blood vessels is obtained. Consequently, at the time of insertion simulation of medical instruments or fluid, a blood vessel model having a membranous structure inside the three-dimensional model can change its shape with flexibility in the base material similar to the blood vessel in the living body, and so the blood vessel model is suitable for replicating the shape-changing property of the blood vessel of the living body.

Herein, the membranous model can be obtained by laminating a membranous model molding material onto the above-mentioned body cavity model thinly and hardening thereof.

The membranous model molding materials are not particularly limited as long as they are isotropic materials exhibiting a photoelastic effect. For example, in addition to elastomer such as silicone rubber (silicone elastomer) and thermosetting polyurethane elastomer, and the like, thermosetting resin such as silicone resin, epoxy resin, polyurethane, unsaturated polyester, phenol resin, urea resin, and the like, and thermoplastic resin such as polymethyl methacrylate and the like can be used alone or in combination thereof. These materials are laminated thinly on the surface of the body cavity model by the method of coating, spraying, dipping, or the like, and then cured or hardened by the well-known method.

When the target of the membranous model is a cerebral blood vessel, it is preferable to employ materials having high transparency, and elasticity and flexibility similar to those of living tissues. An example of such materials can include silicone rubber. Furthermore, since silicon rubber has a contact property similar to that of the living tissue, it is suitable for insertion of a medical instrument such as a catheter and carrying out an operation.

The membranous model molding materials may be formed of plural layers. The thickness thereof may be determined arbitrarily.

It is preferable that the membranous model is formed so that the entire model has a substantial uniform thickness from the viewpoint of observing a photoelastic effect.

As a base material, a translucent material having a physical property similar to that of the living body is preferably used.

Herein, the living tissue signifies a flexible tissue surrounding a blood vessel and the like replicated by a membranous model. As such base materials having flexibility (physical properties), in Examples, a silicone gel and a glycerine gel are used. Gelatin, agar, polysaccharide gel, and the like, can be used. Note here that liquid with high viscosity can be used as a base material as long as the casing can secure the air-tightness.

When gel is used as a material of the base material, by using a plurality of materials with different physical properties, the base material can be approached to the living tissues.

In order to observe the dynamic behavior of the membranous model, the base material is preferably translucent. In order to clarify the boundary between a membranous model and a base material, at least one of the membranous model and the base material can be colored. Furthermore, in order to observe the dynamic behavior of the membranous model more exactly, it is preferable that the refractive index of the material of the membranous model is substantially the same as that of materials of the base material.

The entire part of the membranous model is not necessarily embedded in the base material. That is to say, a part of the membranous model may be located in a gap. Furthermore, a part of the membranous model may be located in a solid base material (having a physical property that is not similar to that of the living tissues).

The base material is allowed to have elasticity. Preferably, the base material is a low-elastic material having elastic modulus of 2.0 kPa to 100 kPa. More preferably, the base material has sufficient elongation. Thus, even if the membranous model is largely deformed, a base material is not peeled off from the membranous model. It is preferable that when the base material is stretched while adhesiveness with respect to the membranous model is secured, the base material shows 2 to 15 times elongation rate as the elongation rate of 1 when no load applied. Herein, the elongation rate denotes a maximum deformation amount in which the base material can return to the original state. Furthermore, it is preferable that the speed at which the base material returns to the original state when load is removed from the base material, which was deformed while applying load, is relatively gentle. For example, loss factor tan $\delta$ (at 1 Hz) as a viscoelastic parameter can be 0.2 to 2.0.

Thus, the base material has the property that is the same or near property as the tissues existing around blood vessels and the like and the membranous model is deformed in the environment that is more similar to the actual environment. That is to say, the feeling of insertion of a catheter and the like can be realized more realistically.

The base material is allowed to have adhesiveness with respect to the membranous model. Thus, even if the membranous model is deformed when a catheter, and the like, is inserted into the membranous model, no dislocation occurs between the base material and the membranous model. The dislocation occurred therebetween makes the stress applied to the membranous model vary. It causes, for example, confusion of an insertion simulation of a catheter and therefore indisposition feeling may occur as the catheter is inserted When the membranous model is a model of the cerebral blood vessels, it is preferable that the adhesiveness (adhesive strength) between the base material and the membranous model is in the range from 1 kPa to 20 kPa.

As such base materials, in Examples, a silicone gel and a glycerine gel are used, but the material is not particularly limited to them. Note here that liquid with high viscosity can be used as a base material as long as the casing can secure the air-tightness. This is particularly suitable as a base material for a membranous model replicating blood vessels surrounded by living tissues without having elasticity. By mixing these plural kinds of fluids and further mixing an adhesive agent thereto, a suitable base material can be prepared.

When gel is used as a material of the base material, by using a plurality of materials with different physical properties, the base material can be approached to the living tissues.

In order to observe the dynamic behavior of the membranous model, the base material is preferably translucent. In order to clarify the boundary between a membranous model and a base material, at least one of the membranous model and the base material can be colored. Furthermore, in order to observe the dynamic behavior of the membranous model more exactly, it is preferable that the refractive index of the material of the membranous model is substantially the same as that of materials of the base material.

The entire membranous model is not necessarily embedded in the base material. That is to say, a part of the membranous model may be located in a gap. Furthermore, a part of the membranous model may be located in a solid base material (having a physical property that is not similar to that of the living body) or in fluid.

Casing accommodates a base material and may have any shapes. Entire or a part of the casing is formed of a translucent material so that the dynamic behavior of the membranous model can be observed. Such a casing can be formed of a translucent synthetic resin (an acrylic plate, and the like) and a glass plate.

The casing is provided with a hole communicating to a cavity of a membranous model. A catheter can be inserted from this hole.

It is preferable that an entire three-dimensional model is translucent. From the viewpoint of observing the state in which a catheter is inserted, at least the inside of the membranous model may be visually recognized.

A sufficient distance is provided between the casing and the membranous model. Thus, a sufficient margin (thickness) is secured with respect to a base material having elasticity. When an external force is applied to the membranous model by the insertion of a catheter and the like, the membranous model can change its shape freely based on the external force. Note here that this margin can be selected arbitrarily in accordance with the subject of the three-dimensional model, application of use, and the like, however, for example, it is preferable that the margin is not less than 10 to 100 times as the film thickness of the membranous model.

A core in a state in which a body cavity model is covered with a membranous model is set in a casing and a base material is infused in the casing and gelled.

Thereafter, when a body cavity model is removed, a membranous model remains in the base material.

A method of removing the body cavity model may be appropriately selected in accordance with the shaping material of the body cavity model. It is not particularly limited as long as the method does not affect other materials of the three-dimensional model.

As the method of removing the body cavity model, (a) a heat melting method of melting by heating; (b) a solvent melting method of melting by a solvent; and (c) a hybrid method combining melting by heating and melting by a solvent, and the like, can be employed. By these methods, the body cavity model is removed by selectively fluidizing and eluting out the body cavity model to the outside of the three-dimensional model.

A part of the component of materials of the body cavity model diffuses to the inside of the membranous model. This diffusion may cause fogging in the membranous model to lower the recognition property. In order to remove this fogging, it is preferable that the sample is heated again after the body cavity model is removed. This heating may be carried out in the middle of removing the body cavity model.

This three-dimensional model may be also formed by the following method.

The body cavity model as a core is embedded in a gel-like base material and then the body cavity model is removed. Thus, a cavity replicating the body cavity is formed in the base material. Thereafter, a forming material of the membranous model is attached to the peripheral wall of the cavity and then hardened by polymerization or curing, and the like. The formation material of the membranous model is poured into the cavity in the base material or by dipping the base material into the formation material of the membranous model, the formation material of the membranous model can be attached to the peripheral wall of the body cavity of the base material.

Furthermore, instead of attaching the forming material of the membranous model to the peripheral wall of the cavity, the peripheral wall of the cavity can be treated to have a hydrophilic property. Thus, when water or an aqueous solution is infused in the cavity of the three-dimensional model, a water membrane is formed on the peripheral wall and insertion resistance of a catheter is reduced. That is to say, this water membrane corresponds to the membranous model.

In the case where the peripheral wall of the cavity is treated to have a hydrophobic property (lipophilic property), similarly, when oil is infused in the cavity, an oil membrane is formed on the peripheral wall and insertion resistance of a catheter is reduced. That is to say, this oil membrane corresponds to the membranous model.

The peripheral wall of the cavity can be made to be hydrophilic or hydrophobic by the well-known method. For example, when a silicon gel is used as a base material, by forming a film having a polar group such as a surfactant on the peripheral wall, the peripheral wall of the cavity can be made to be hydrophilic. Similarly, by forming an oil film such as oil, wax, or the like, on the peripheral wall of the cavity, the peripheral wall of the cavity can be made to be hydrophobic.

The base material of the body cavity model is formed of a translucent gel material such as silicone rubber and the like, and the entire or a part of the peripheral wall of the body cavity portion may be covered with a material having a modulus of photoelasticity that is higher than that of the gel material. A material having a higher modulus of photoelasticity may be embedded in the base material. Thus, the photoelastic effect can be emphasized by a material having a higher modulus of photoelasticity. Note here that an example of the material having a higher modulus of photoelasticity can include epoxy resin, and the like. The thin film of epoxy resin can be easily deformed by the insertion of a catheter. Therefore, the use of epoxy resin makes it possible to observe the photoelastic effect clearly.

Casing accommodates a base material and may have any shapes. Entire or a part of the casing is formed of a translucent material so that the dynamic behavior of the membranous model can be observed. Such a casing can be formed of a translucent synthetic resin (an acrylic plate, and the like) and a glass plate.

The casing is provided with a hole communicating to a cavity of a membranous model. A catheter can be inserted from this hole.

It is preferable that an entire three-dimensional model is translucent. From the viewpoint of observing the state in which a catheter is inserted, at least the inside of the membranous model may be visually recognized.

(Photoelastic Effect)

"A photoelastic effect" means that when internal stress is generated in translucent material, temporary birefringence occurs so as to make difference in the refractive index between the direction of maximum principal stress and the direction of minimum principal stress, so that incident light progresses in a state in which it is divided into two plane polarized lights. The phase difference in the two waves allows interference fringe to be generated. By observing this interference fringe, it is possible to know the state of the internal stress of the translucent material.

In order to produce this photoelastic effect, as shown in FIG. 1, light from a light source is allowed to pass through a first polarizing plate (polarizing filter) to be polarized and this linear polarized light is allowed to pass through a three-dimensional model. When the internal stress is generated in the three-dimensional model, the birefringence is generated in accordance with the strength of the internal stress, and the maximum principal stress ($a\cos\phi \sin \omega t$) and the minimum principal stress ($a\cos\phi \sin(\omega t\text{-}A)$) are generated. Since these lights are different in speed, phase difference occurs. When these lights are observed through a second polarizing plate (polarizing filter), interference fringe appears. Note here that the polarization direction of the second polarizing plate is substantially orthogonal to the polarization direction of the first polarizing plate.

Examples of the method of observing the photoelastic effect generated in light passing through a three-dimensional model that is allowed to intervene between a pair of polarizing plates include an orthogonal Nicol method, a parallel Nicol method and a sensitive color method, and the like. Furthermore, as a method of detecting a photoelastic effect, by intervening a pair of ¼ wavelength plates (¼ wavelength filters) between the polarizing plate and the three-dimensional model, a circular polarizing method, a Senarmont method, and the like, are known.

Thus, by using a photoelastic effect, it is possible to observe the change of stress in a region around the cavity when a catheter is inserted into the cavity of the three-dimensional model. However, since the catheter itself does not generate any photoelastic effect, the position and a state cannot be observed together with the photoelastic effect accompanied with the change of stress in the region around the catheter.

Therefore, in the present invention, a phase shift filter is allowed to intervene in the first polarizing filter at the side of the light source and the second polarizing filter at the side of an observer, which makes it possible to observe the position and state of the catheter itself. That is to say, by intervening the phase shift filter, a part of light passing through the first polarizing filter passes through the second polarizing filter, and constitutes the background light. Herein, when a catheter exists in the three-dimensional model, it appears as a shadow, the position, state and operation can be observed. That is to say, it is possible to observe a catheter and photoelastic effect generated by the catheter simultaneously.

As a phase shift filter, it is preferable to use a phase shift filter capable of shifting the light passing through the first polarizing filter by one or two wavelength. It is advantageous because the sensitivity of the photoelastic effect can be improved.

In the present invention, a plurality of wavelength shift filters may be used as long as background light can be taken out from the second polarizing filter at the side of an observer. Note here that in a circular polarizing method, a Senarmont method and the like, a ¼ wavelength plate is used. However, since in such methods, background light cannot be taken out from the second polarizing filter, it is not possible to observe a catheter.

The phase shift filter can be designed in an arbitrary thickness or shape. For example, it may be formed in a sheet shape, a plate shape, and the like.

Also with the use of a parallel Nicol method, it is possible to observe the shadow of the catheter and the photoelastic effect. This is because when a polarizing filter is disposed in a non-orthogonal state with respect to a polarized light source, a part of light from the polarized light source passes through the polarizing filter.

Note here that although the observation of the photoelastic effect by this parallel Nicol method has low sensitivity, the configuration thereof can be simplified as compared with the type in which the phase shift filter is allowed to intervene.

From the investigation of the present inventors, it is preferable that a phase shift filter is disposed between the second polarizing filter at the observation side and the ¼ wavelength filter, and the phase shift filter is allowed to be tilted at approximately 22.5° with respect to an optical axis of the ¼ wavelength filter.

Figure 2:
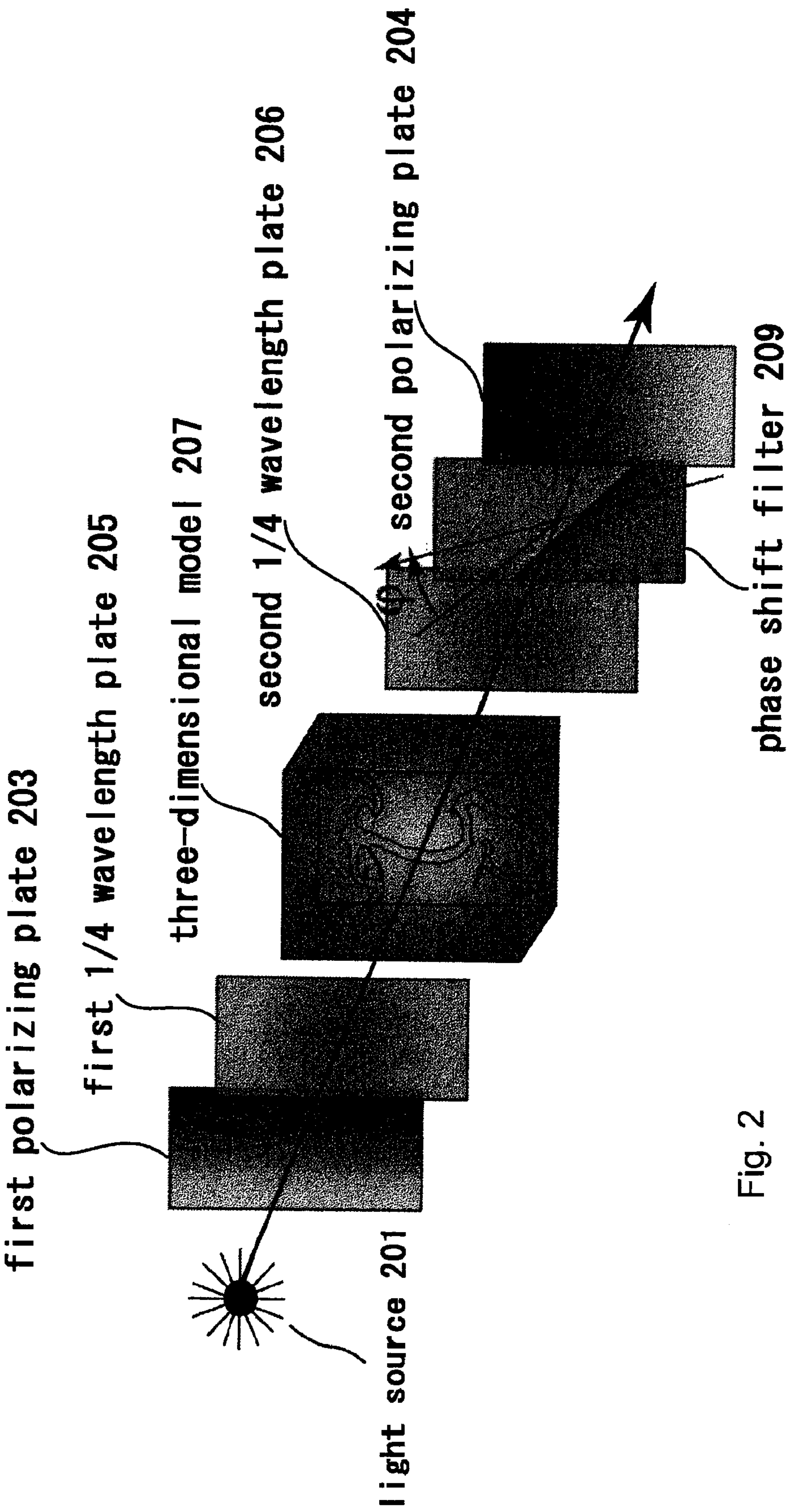
FIG. 2 is a schematic view showing a configuration of a simulator in accordance with one aspect of the present invention.

Such a configuration is shown in FIG. 2. In FIG. 2, reference numeral 201 denotes a white light source; 203 and 204 denote a polarizing filter; 205 and 206 denote a ¼ wavelength filter; 207 denotes a three-dimensional model that is a target of the observation, and 209 denotes a phase shift filter (in this example, two-wavelength plate).

When the tilt angle ϕ of the phase shift filter 209 is in the range from ±5° to ±40°, more preferably, when the tilt angle ϕ is ±22.5°, from the photoelastic effect (light color (wavelength)) to be observed in the second polarizing filter 204, the stress of the observation target and the direction thereof can be specified.

The reason thereof is described below.

In the configuration shown in FIG. 2, the strength I of the light to be observed is expressed by the following equation 1.

[Equation 1]

$$I = 4c_1^2c_2^2\sin^2(Re_{ex}/2)\cos^2(Re/2) + \{c_1^4 + c_2^4 + 2c_1^2c_2^2\cos(Re_{ex}/2)\}\sin^2(Re/2) + c_1c_2\sin Re\{(c_1^2 - c_2^2)\sin 2\theta - c_1^2\sin(2\theta - Re_{ex}/2) + c_2^2\sin(2\theta + Re_{ex}/2)\} \quad (1)$$

$$c_1 = \sin\varphi,$$
$$c_2 = \cos\varphi$$

Herein, θ denotes the direction of stress and Re denotes retardation by the phase shift generated by the photoelastic effect. Note here that this Re corresponds to the strength of stress.

Figure 3:
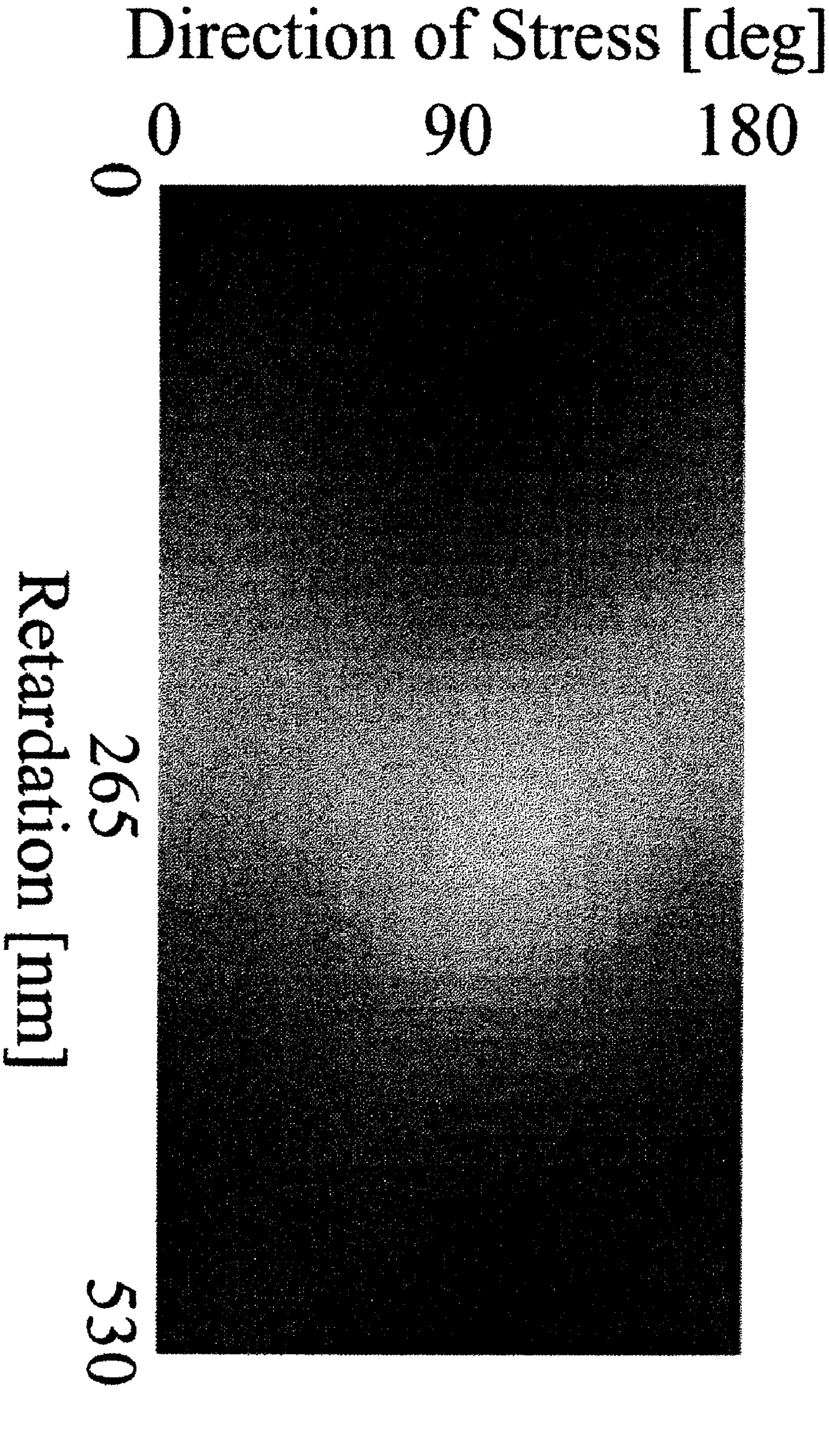
FIG. 3 shows a color map obtained by the simulator shown in FIG. 2 when $\phi$ is 22.5°.

When ϕ is 22.5° and each wavelength of RGB is substituted in the above-mentioned equation 1, the color (wavelength) of light to be observed reflects the direction of stress and the strength of stress. In other words, from the color of the observed light, the direction of stress and the strength of stress can be specified. The relation between the observed light and the direction of stress and the strength of stress is shown in the map of FIG. 3. Note here that, when printed in paper, FIG. 3 is shown in black and white. Actually, however, the change of color can be observed over the entire region of FIG. 3. In FIG. 3, a color (wavelength) specified by an arbitrary coordinate of ordinate (direction of stress) and an arbitrary coordinate of abscissa (strength of stress) is specified to substantially one color (wavelength). Such a color map can be obtained when ϕ is in the range from ±5° to ±40°. More clear color map can be obtained when ϕ is ±22.5°.

Figure 4:
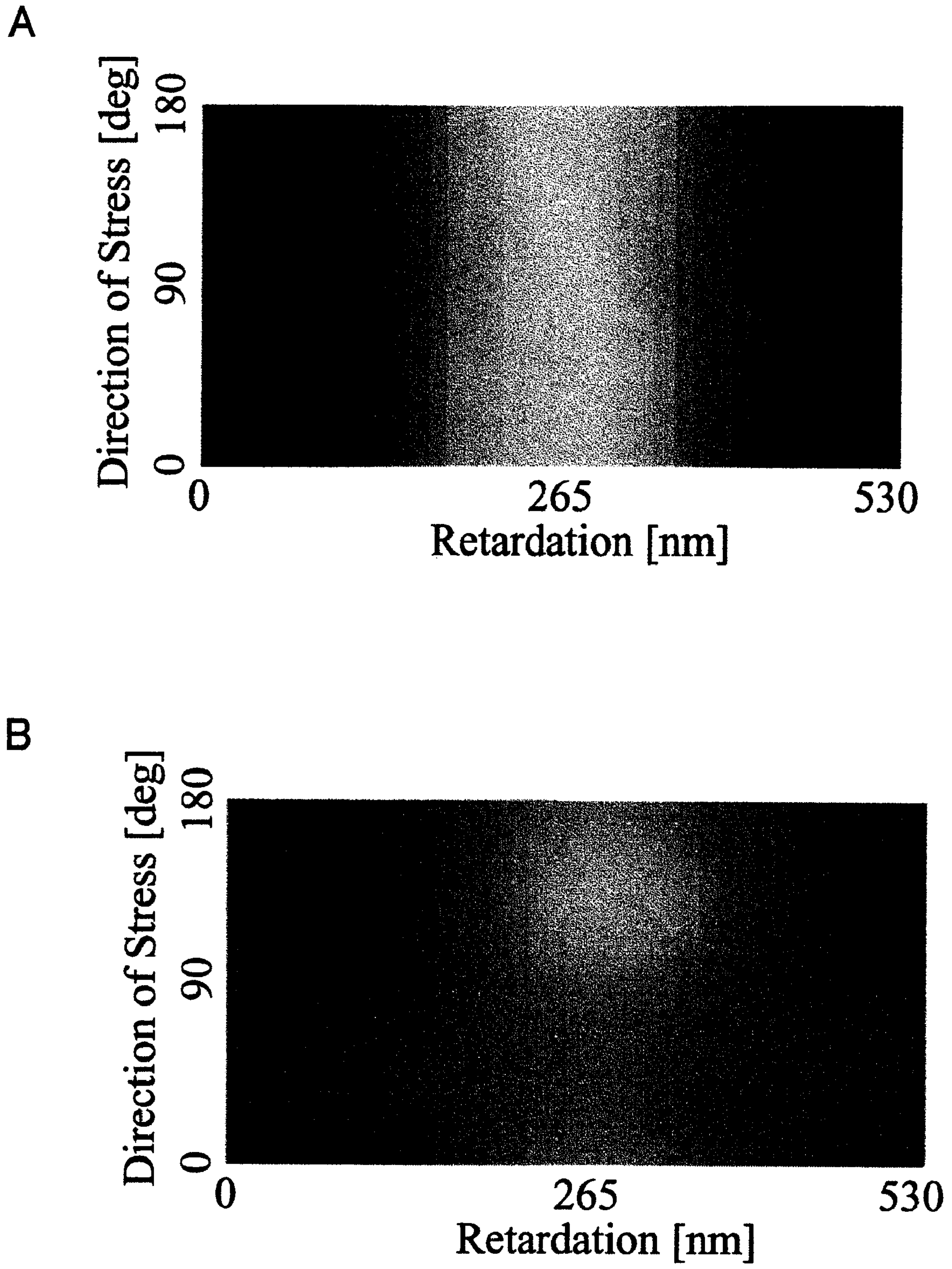
FIG. 4 shows color maps obtained by the simulator shown in FIG. 2 when $\phi$ is 0° and $\phi$ is 90°.

On the other hand, when ϕ is 0°, or ϕ is 90°, as shown in FIG. 4A, since the color is distributed vertically symmetric with respect to 90° of the ordinate, it is not possible to specify the direction of stress or the strength of stress from the observed color. Furthermore, when ϕ is ±45°, as shown in FIG. 4B, since it is not possible to obtain the effect of the phase shift filter, it is difficult to observe the shadow of the catheter.

Furthermore, according to the investigation of the present inventors, under ϕ is ±22.5°, when the light source is G (green color) light, in the map of FIG. 3, it is shown that brightness (strength) of green color is distributed corresponding to the abscissa. Actually, the brightness is the strongest in the center of the abscissa and the brightness reduces in accordance with the movement to left and right. The maximum stress according to the three-dimensional model corresponds to about Re=265 to 400. When the stress is beyond the range, damage may occur. Therefore, when focused on the brightness of green color, strength of stress applied to the three-dimensional model can be specified. An operator can know the state of stress of the three-dimensional model when a catheter surgery simulation is carried out real time and intuitively.

Furthermore, in the present invention, as a light source, a display device is used.

When a display device is used as a light source, colors of emitted light can be arbitrarily set by controlling the display device by a control device. Furthermore, it is possible to switch colors of emitted light in a simple and rapid way. In addition, since the display can display still images and moving images, when the images on the display and the photoelastic effect are observed in a way in which they are superimposed to each other, the display can provide a larger amount of information to an observer.

It is preferable to use a liquid crystal display as a display device. It is advantageous because the liquid crystal can release polarized light, so that the first polarizing filter can be omitted.

Needless to say, CRT, plasma display, and other generally used display devices can be employed. In a type that cannot release polarized light, it is necessary to polarize the light from the light source of the display device by using the first polarizing filter.

It is preferable that this display device can release all of RGB colors. It is advantageous because colors of light to be emitted can be set arbitrarily.

The display device is provided with a control device. This control device enables arbitrary images to be displayed on the display device. Examples of the image include still images such as patterns, characters, figures, pictures, and the like, as well as moving images. More specifically, numerical information or graph showing the strength or direction of the stress applied to the three-dimensional model, or figures or patterns indicating a specific targeted region on the three-dimensional model, or image or picture showing the inside of the body for enhancing presence of a catheter surgery simulation, or navigation pictures for training a catheter surgery, or picture information of a doctor in remote location, which is obtained via network, or color patterns for selectively extracting the specific photoelasticity information, or the like.

EXAMPLES

First Example

In order to obtain three-dimensional data regarding the shapes of cerebral blood vessels and affected sites, such as cerebral aneurysm to be targets of a three-dimensional model, a head portion of a patient was photographed with a helical scanning X-ray CT scanner having spatial resolution of 0.35×0.35×0.5 mm while administering contrast media into the blood vessels of the region to be imaged. The three-dimensional data obtained by photographing were reconstructed into 500 pieces of 256-gradation two-dimensional images (tomographic data) having a resolution of 512×512 which were arranged in equal intervals along the body axis so that they are passed to a three-dimensional CAD software, and then image data corresponding to respective two-dimensional images were preserved in a 5.25-inch magneto-optical disk by a drive incorporated in the X-ray CT scanner in the order according to the imaging direction.

Then, by a 5.25-inch magneto-optical drive externally connected to a personal computer, the image data were taken into a storage device in the computer. From these image data, three-dimensional shape data having an STL format (format in which a three-dimensional curved surface is represented as an assembly of triangle patches), which are necessary for laminate shaping, were generated by using a commercially available three-dimensional CAD software. In this conversion, by laminating input two-dimensional images based on the photographing intervals, a three-dimensional scalar field having an intensity value as a scalar amount is constructed and a specific intensity value giving the inner surface of the blood vessels is specified on the scalar field, and thereby three-dimensional shape data of lumen of blood vessel lumens are constructed as an isosurface (boundary surface of specific scalar value). Then, rendering approximating to triangle polygon is carried out with respect to the constructed isosurface.

Figure 5:
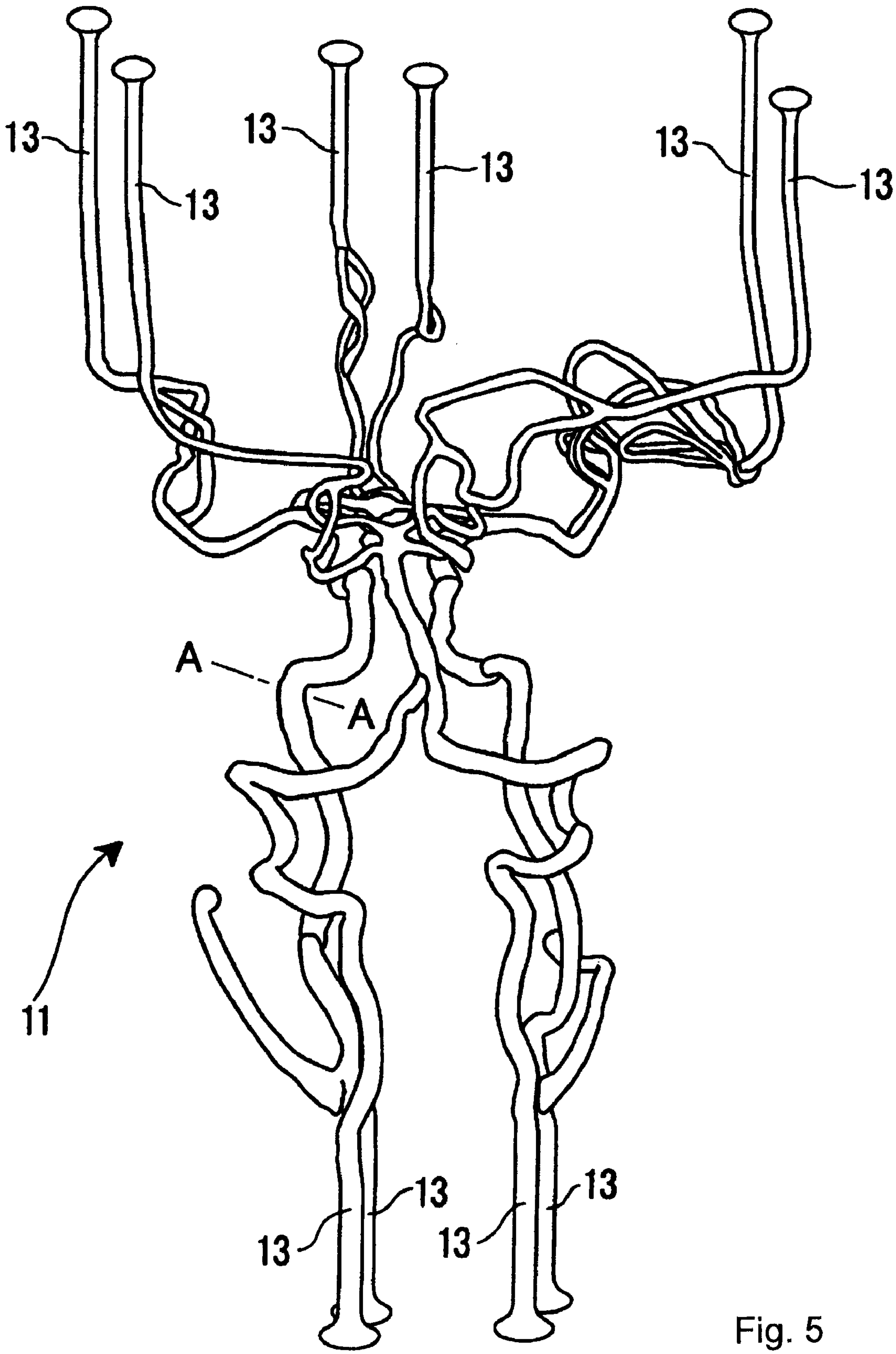
FIG. 5 is a perspective view showing a core 11 of an Example.
Figure 6:
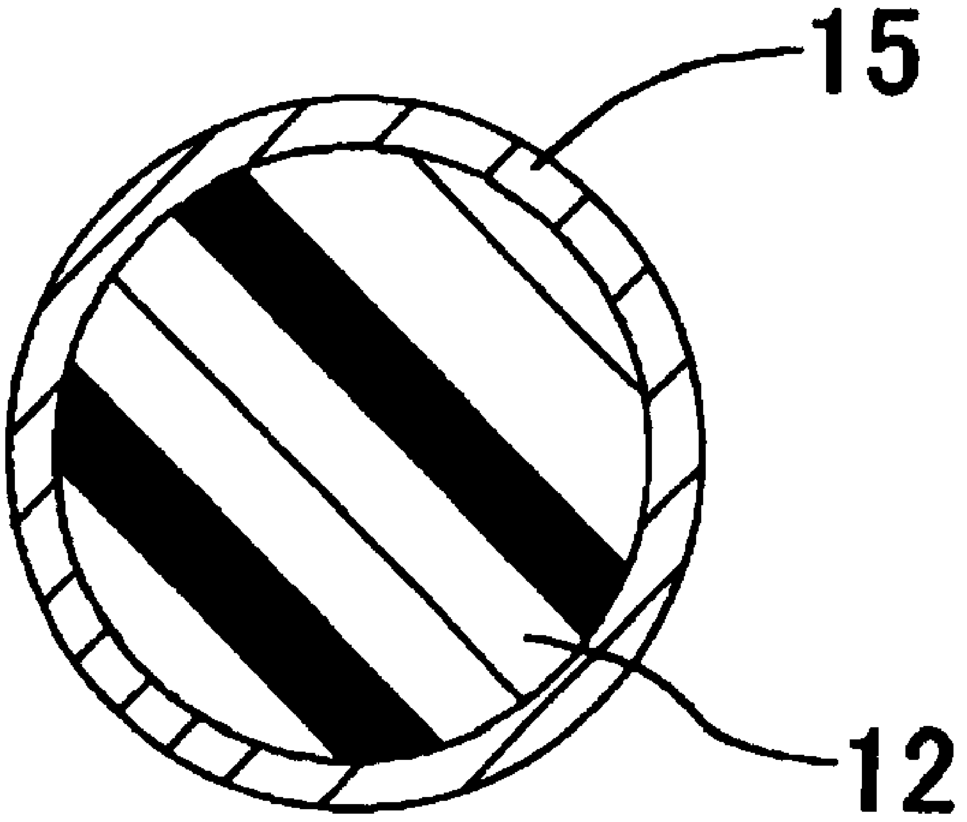
FIG. 6 is a cross-sectional view taken on line A-A of FIG. 5, showing the configuration of the core.

Note here that additional data were added to the three-dimensional shape data in this stage and a guide portions 13 were expanded and protruded (see FIG. 5) from the end of the body cavity model 12 (see FIG. 6). This guide portion 13 is a hollow columnar member. By providing a hollow portion 31, the time required for laminate shaping is shortened. A tip portion of this guide portion 13 has a large diameter and this portion is extended out to the surface of the three-dimensional model to form a large diameter opening 25 (see FIG. 6).

The generated three-dimensional shape data having an STL format were then transferred to a laminate shaping system carrying out a melted resin jet method, and the arrangement, the laminating direction and the laminating thickness of a model in the laminate shaping system were determined, and at the same time, a support was added to the model.

The thus generated data for laminate shaping were sliced to the predetermined laminate shaping thickness (13 μm) to generate a large number of slice data on a computer. Then, based on each of thus obtained slice data, a shaping material (melting point: about 100° C., easily dissolved in acetone) containing p-toluensulfonamide and p-ethylbenzene sulfonamide as main components was melted by heating and allowed to be ejected Thereby, a resin hardened layer with specified thickness having a shape corresponding to each of the slice data was formed and laminated on a one-by-one basis. Thus, laminate shaping was carried out. By removing a support after the last layer was formed, a laminate shaping model (body cavity model 12) of a region of cerebral blood vessel lumens was formed.

Furthermore, the surface of the body cavity model 12 is treated to be smooth.

The silicone rubber layer 15 was formed on the entire surface of the body cavity model 12 in the thickness of about 1 mm (see FIG. 6). This silicone rubber layer 15 is obtained by dipping the body cavity model 12 in a silicon rubber bath, taking it out, and drying while rotating the body cavity model. This silicone rubber layer becomes a membranous model.

In this Example, the entire surface of the body cavity model 12 was coated with the silicone rubber layer 15. However, a predetermined portion of the body cavity model 12 can be coated with the silicon rubber layer 15 partially.

A core 11 obtained by coating the body cavity model 12 with a membranous model formed of the silicone rubber layer 15 is set in a rectangular parallelepiped casing 24. This casing 24 is formed of a transparent acrylic plate. Into the casing, a material of a base material 22 is infused and gelled.

As a material for the base material 22, two-liquid mixing type silicone gel was used. This silicone gel has transparency and elasticity. Moreover, it has a physical property that is extremely similar to the soft tissues around the blood vessels. Polycondensation type silicone gel can be also used. Thus, the base material has a translucent property and elasticity and has an adhesive property with respect to a membranous model.

The physical property of the material of the base material 22 is adjusted to be matched to the physical property of the tissues around the blood vessels that are subject of the membranous model.

Note here that in this Example, by using penetration, fluidity, stickiness, stress relaxation property, and the like, as an index, and finally using the touch (feeling of insertion of the catheter) by an operator, the physical property is allowed to approach that of the living body tissue.

In the case of a silicone gel, it is possible to prepare the polymer skeleton and furthermore, by mixing silicone oil, the physical property can be adjusted.

In addition to a silicone gel, a glycerine gel can be used. This glycerine gel is obtained as follows. Gelatin is dipped in water, to which glycerine and phenolate are added, followed by dissolving while heating. While the temperature is high, the mixture is filtrated. When the temperature becomes a temperature that does not affect the core, the mixture is infused and cooled.

Then, the body cavity model 12 inside the core 11 is removed. As the method for removing the body cavity model, a hybrid method was employed. That is to say, a sample is heated and the material of the body cavity model is allowed to flux to the outside from the opening 25. Furthermore, by infusing acetone into the hollow portion so as to dissolve and remove the material of the body cavity model.

Thereafter, the sample was heated in an incubator whose temperature was set to 120° C. for about one hour so as to remove fogging of the membranous model (silicone rubber layer 15).

Figure 7:
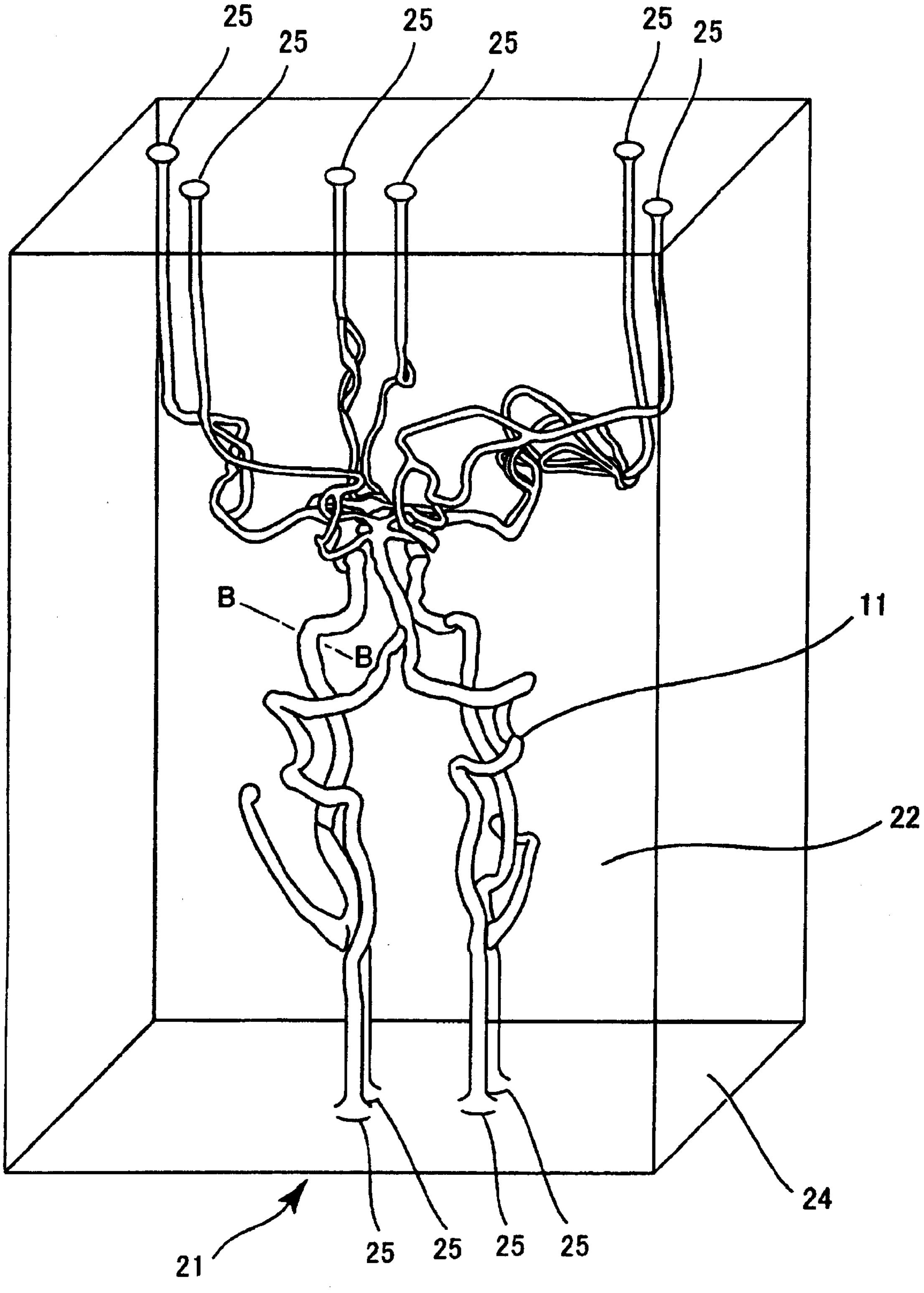
FIG. 7 shows a three-dimensional model in accordance with an Example of the present invention.
Figure 8:
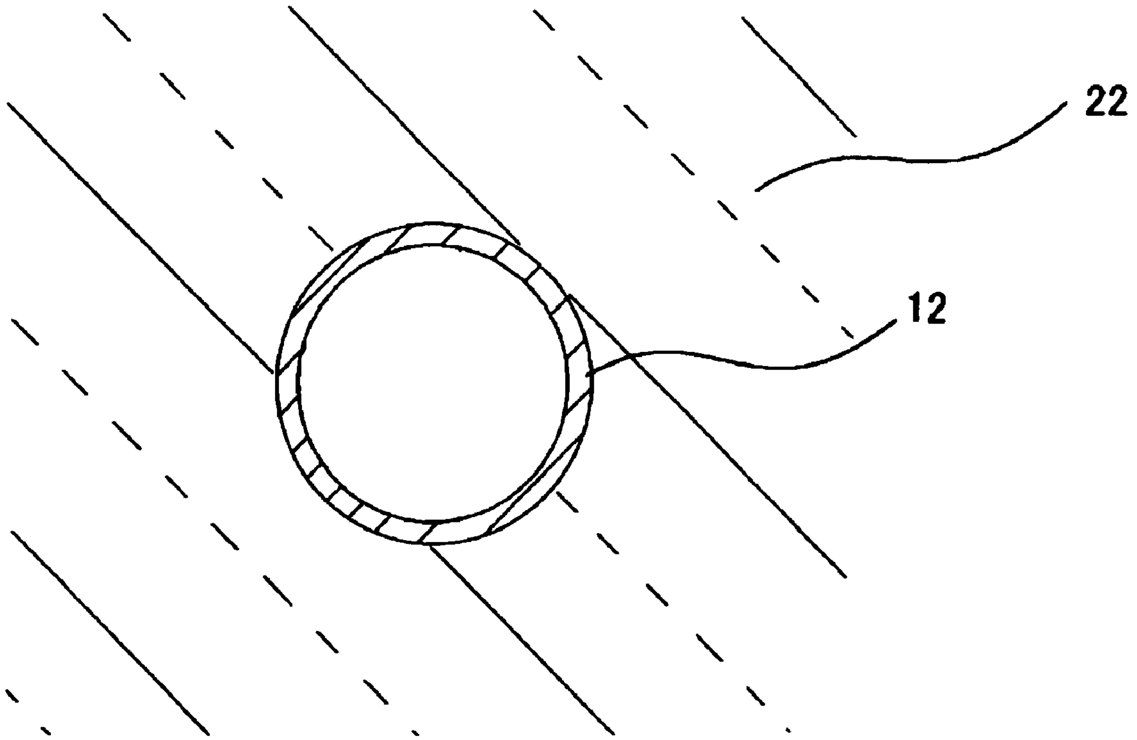
FIG. 8 is a cross-sectional view taken on line B-B of FIG. 7, showing a state in which a membranous model is embedded in a base material.

The thus obtained three-dimensional model 21 has a configuration in which the membranous model 15 is embedded in the base material 22 formed of silicon gel as shown in FIGS. 7 and 8. Since the silicone gel has the physical property similar to the living body tissue, the membranous model 15 shows the dynamic behavior that is the same level as that of the blood vessels.

A three-dimensional model of another exemplary embodiment includes a three-dimensional model obtained by removing the membranous model 15 from the three-dimensional model 21.

In this case, as the base material, it is preferable to use a gelatin having a high modulus of photoelasticity.

Figure 9:
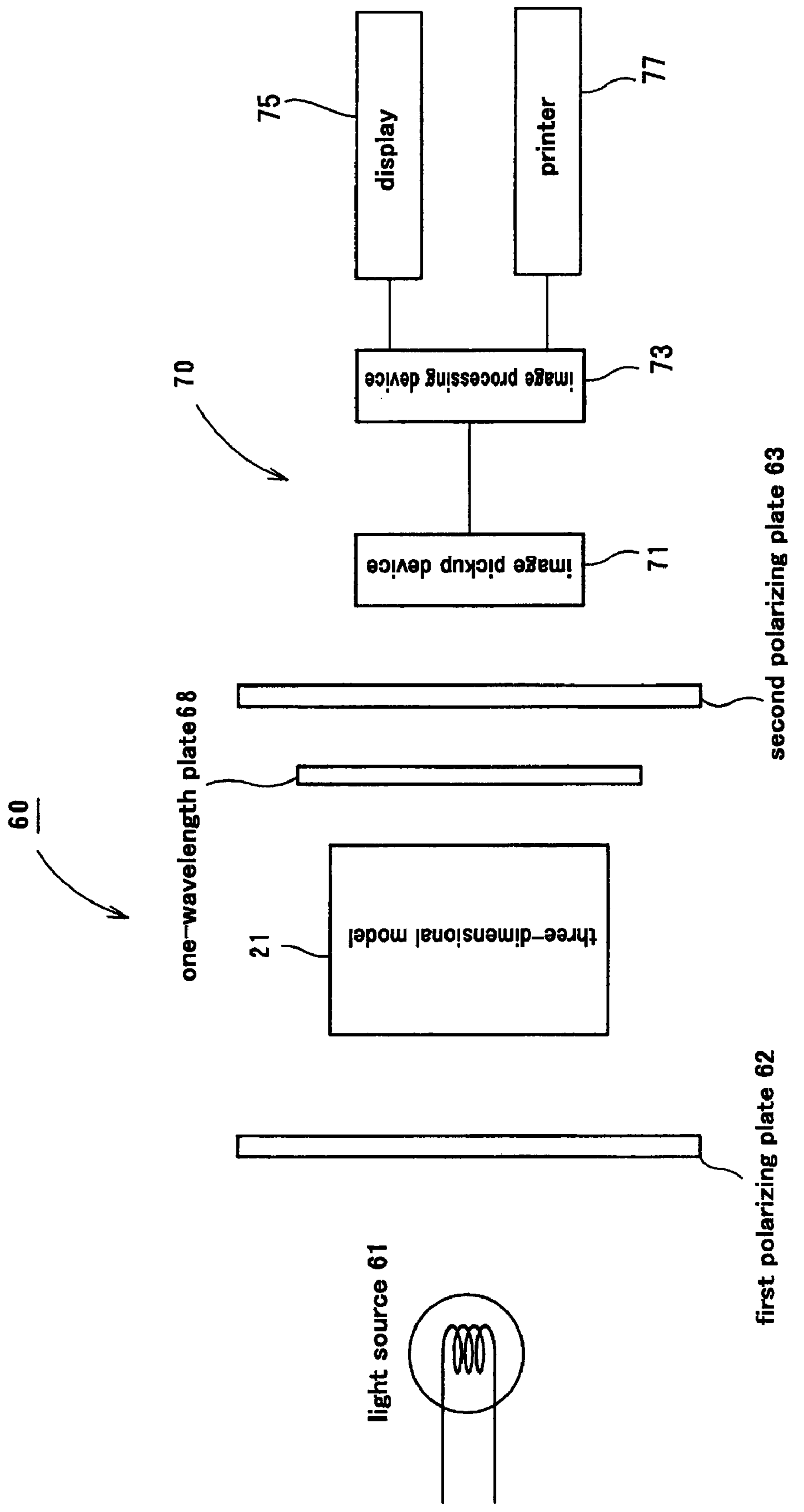
FIG. 9 is a schematic view showing a configuration of a catheter surgery simulator in accordance with an Example of the present invention.

FIG. 9 shows a configuration of a catheter surgery simulator 60 in accordance with an Example of the present invention.

The catheter surgery simulator 60 of this Example schematically includes a light source 61, a pair of polarizing plates 62 and 63, one-wavelength plate 68, three-dimensional model 21 shown in FIG. 7, and photo-receiving portion 70.

It is preferable to use a white light source for a light source 61. Sun light can be used as a light source. Furthermore, a monochromatic light source can be used. The first polarizing plates 62 and 63 have polarization directions which are perpendicular to each other. Thus, the photoelastic effect caused by the internal stress of the three-dimensional model 21 can be observed at the side of the second polarizing plate 63. By intervening the one-wavelength plate 68 between the pair of polarizing plates 62 and 63, light in the vicinity of the wavelength of 530 nm is observed as a background light and materials that do not pass through the second polarizing plate 63, for example, a catheter is observed as a shadow. Note here that the wavelength shift filter represented by the one-wavelength plate 68 may be allowed to intervene between the first polarizing plate 62 and the three-dimensional model 21.

When a catheter is inserted into a cavity of the three-dimensional model 21, when the catheter interferes with the peripheral wall of the cavity, stress is applied to the peripheral wall of the cavity and the photoelastic effect (interference fringe) is generated. Furthermore, from the photoelastic effect, it is possible to simulate the state of stress in a region around the aneurysm accompanied with the deformation of the aneurysm at the time of coil embolization.

In this Example, the light source 61, the first polarizing plate 62, the three-dimensional model 21 and the second polarizing plate 63 were arranged in a line. However, the second polarizing plate 63 may be disposed with deviated (that is to say, displaced from the line). This is because light is reflected diffusedly in the cavity of the three-dimensional model 21, depending upon the shape of the cavity, when the second polarizing plate 63 is deviated, the photoelastic effect may be observed more clearly.

A photo-receiving portion 70 includes an image pickup device 71 consists of CCD, and the like, an image processing device 70 for processing picture images of a photoelastic effect photographed by the image pickup device 71, as well as a display 75 and a printer 77 for outputting the processing results of the image processing portion 70.

Figure 10:
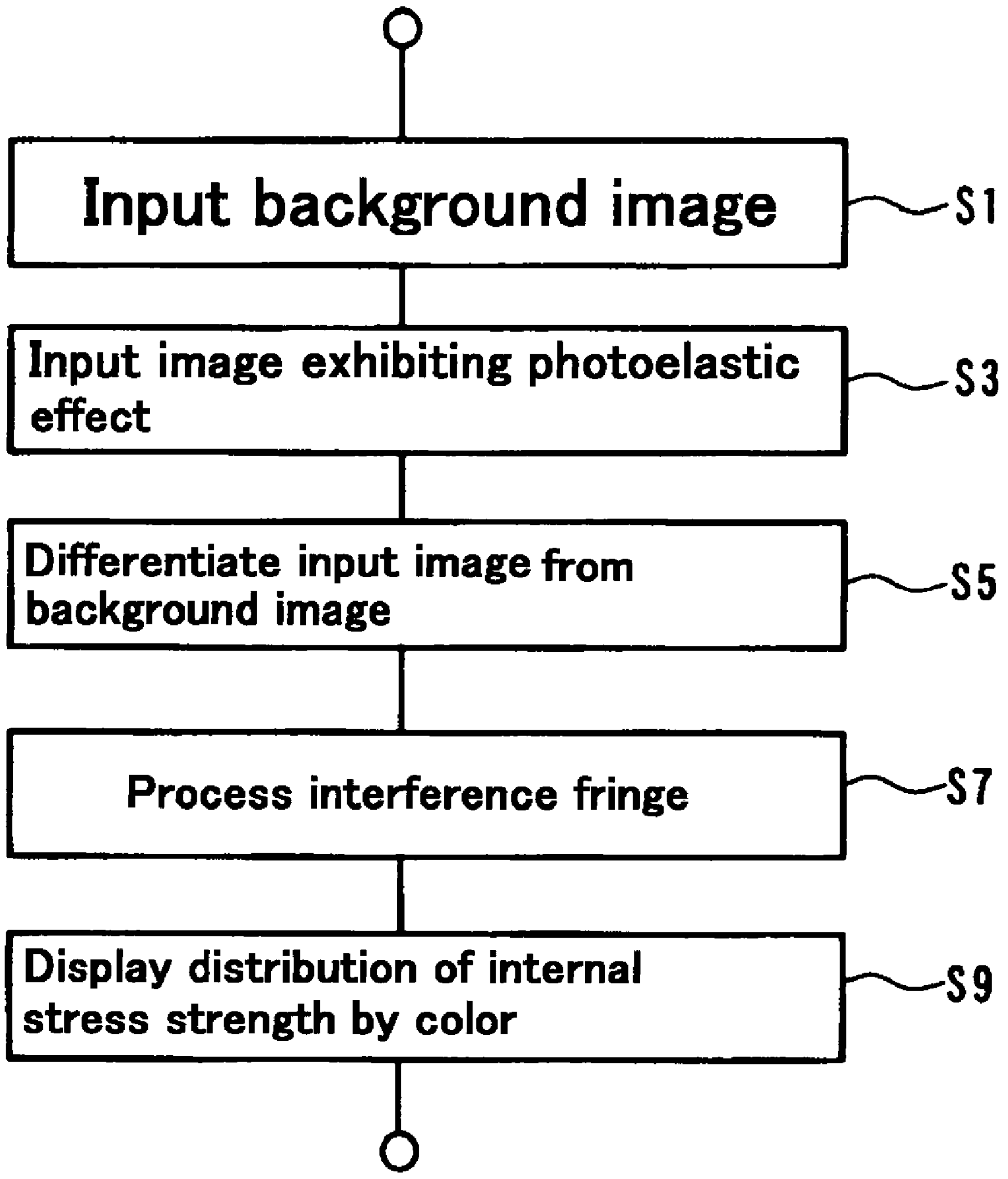
FIG. 10 is a flowchart showing an operation of a photo-receiving portion of the catheter surgery simulator in accordance with an Example of the present invention.

In the image processing device 73, the following processing is carried out (see FIG. 10). Firstly, a picture image in its initial state to which no external force is applied to the three-dimensional model 21 is photographed as a background picture image (step 1). When the three-dimensional model 21 is formed of a material with high modulus of photoelasticity, a photoelastic effect may be generated by self-weight. Therefore, a picture image with interference fringe by the photoelastic effect while light is emitted from the light source 61 and external force is further applied (for example, a catheter is inserted) is input (step 3) and then, the input image is differentiated from the background picture image (step 5).

When the three-dimensional model 21 is formed of a material with high modulus of photoelasticity, dependent upon the internal stress, fine interference fringes appear in a repeating pattern. The image processing device 73 numerically expresses the internal stress by counting the number of patterns per unit area (step 7). Then, in the picture image relating to the shape of the three-dimensional model 21 obtained via a second polarizing plate 63, external display is made by giving a color that corresponds to the values to a portion in which the internal stress is generated (step 9).

In this Example, the photo-receiving portion 70 carries out image processing of interference fringe by the photoelastic effect. However, the interference fringe may be observed by an observer directly or via the image pickup device 71.

Figure 11:
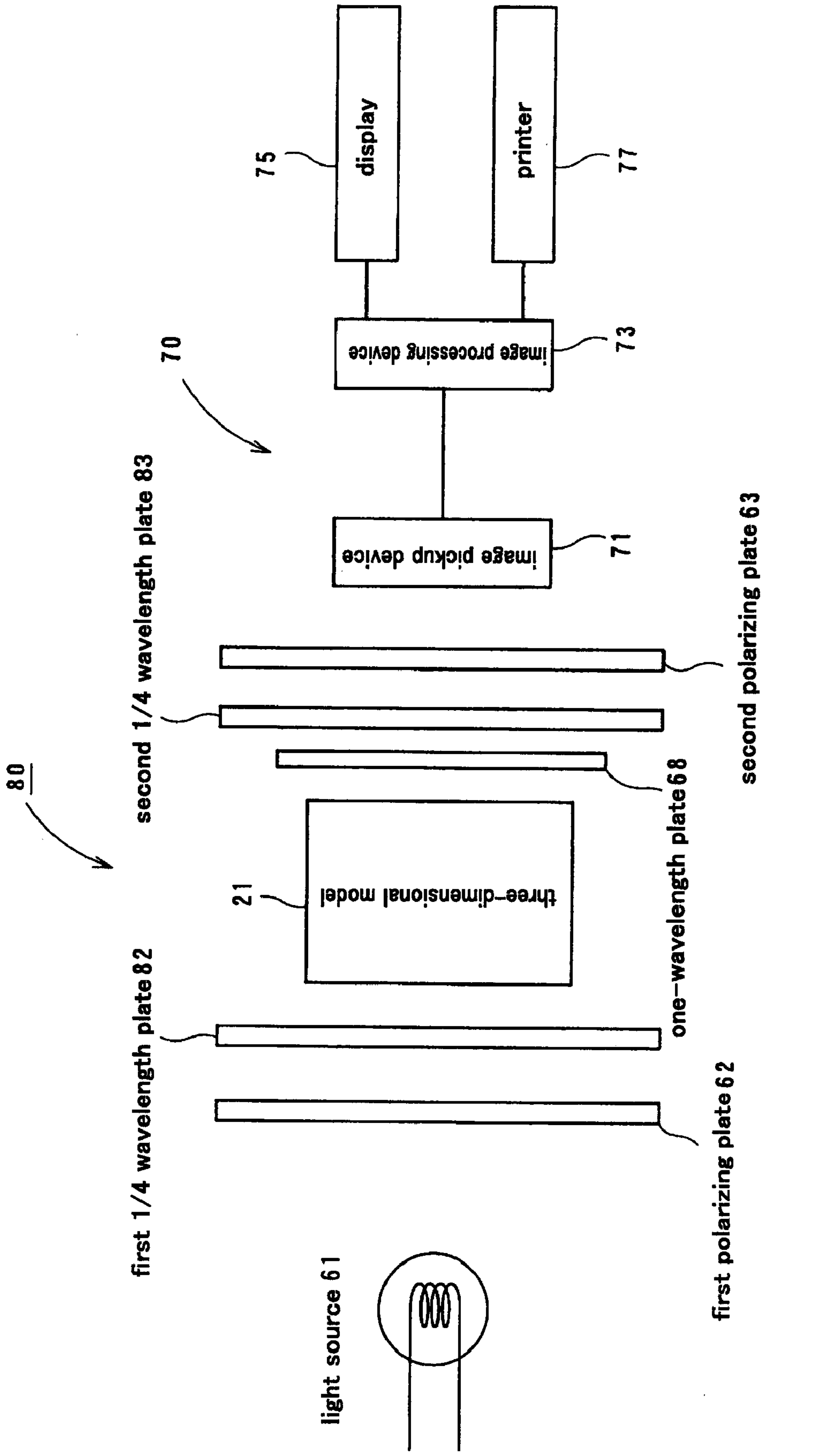
FIG. 11 is a schematic view showing a configuration of a catheter surgery simulator in accordance with another Example of the present invention.

FIG. 11 shows a catheter surgery simulator 80 in accordance with another Example. The same reference numerals are given to the same elements shown in FIG. 12 and description therefor will be omitted herein.

In this Example, between the first polarizing plate 62 and the three-dimensional model 21, a first ¼ polarizing plate 82 is allowed to intervene, and between the three-dimensional model 21 and the second polarizing plate 63, a second ¼ polarizing plate 83 is allowed to intervene. Thus, the photoelastic effect in the three-dimensional model 21 can be observed by the circular polarization method. According to the observation based on the circular polarization method, since the effect in the direction of stress dose not appear in the interference fringe, it becomes easy to control the posture of the three-dimensional model.

In the above-mentioned example, observation was carried out in a state in which the second polarizing plate 62 is allowed to face the image pickup device 71. The observer can carry out observation directly by visual observation.

Figure 12:
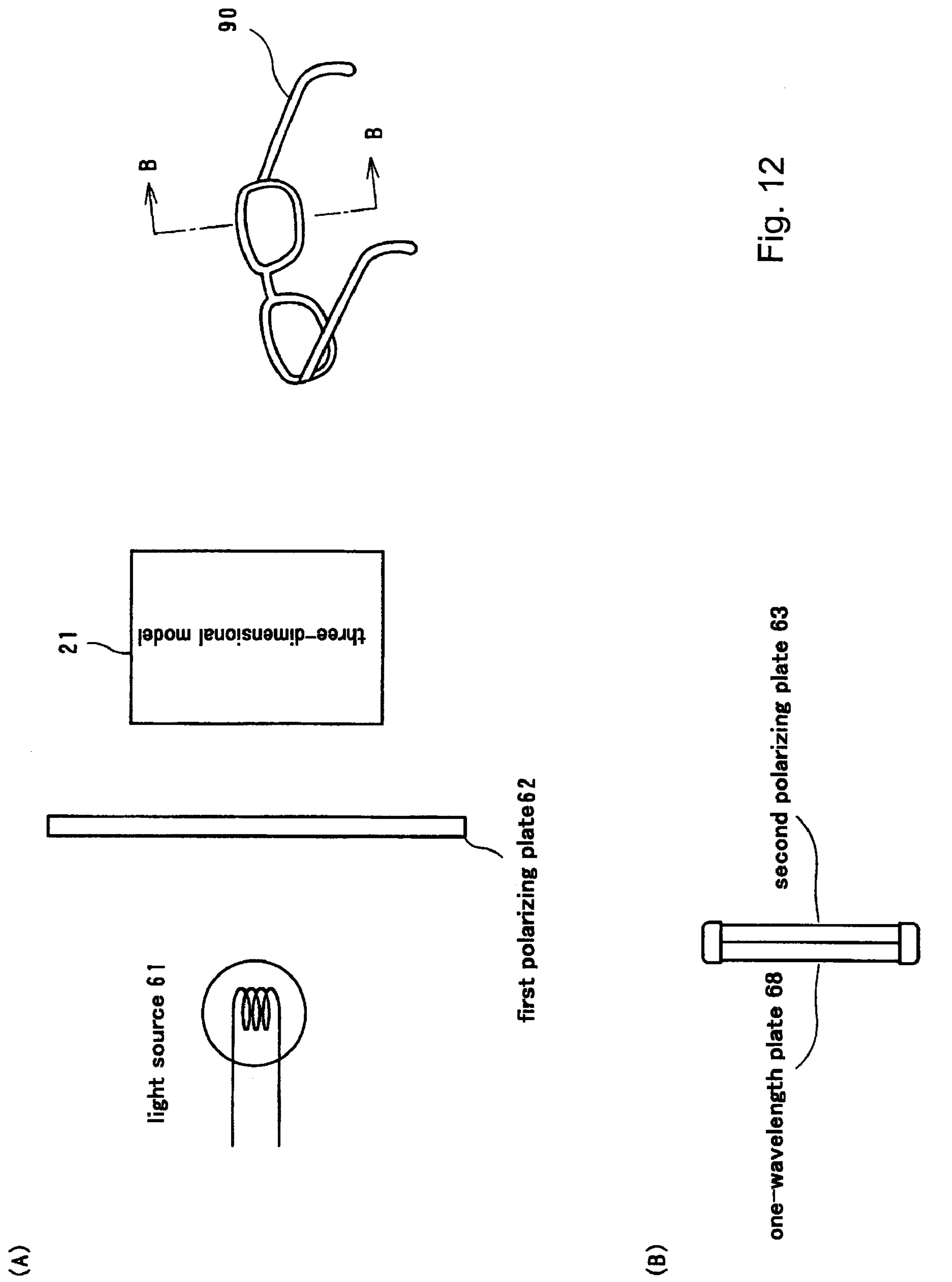
FIG. 12 is a schematic view showing a configuration of a catheter surgery simulator in accordance with another Example of the present invention.

FIG. 12 shows an example suitable for visual observation. In this example, glasses 90 are prepared. Lens portions of the glasses 90 have a two-layered structure. As shown in FIG. 12B, the polarizing plate 63 is disposed at the side of an observer and the one-wavelength plate 68 is disposed outside the polarizing plate 63.

When the light source 61 is turned on without wearing these glasses 90, the three-dimensional model 21 is illuminated with light passing through the first polarizing plate 62 and the state of a catheter or the blood vessel structure and the like can be visually observed. On the other hand, since the configuration shown in FIG. 9 is basically formed, when an observer wears the glasses 90, the observer can observe the state of the catheter and the photoelastic effect corresponding to the state of stress of the three-dimensional model by the catheter simultaneously.

This Example employs glasses 90. However, a plate in which a second polarizing plate and the phase shift filter are laminated from the side of an observer may be prepared.

Furthermore, when a phase shift filter represented by a one-wavelength plate is deposed between the first polarizing plate 62 and the three-dimensional model 21, the lens portion of the glasses may be formed by only the second polarizaing plate.

Figure 13:
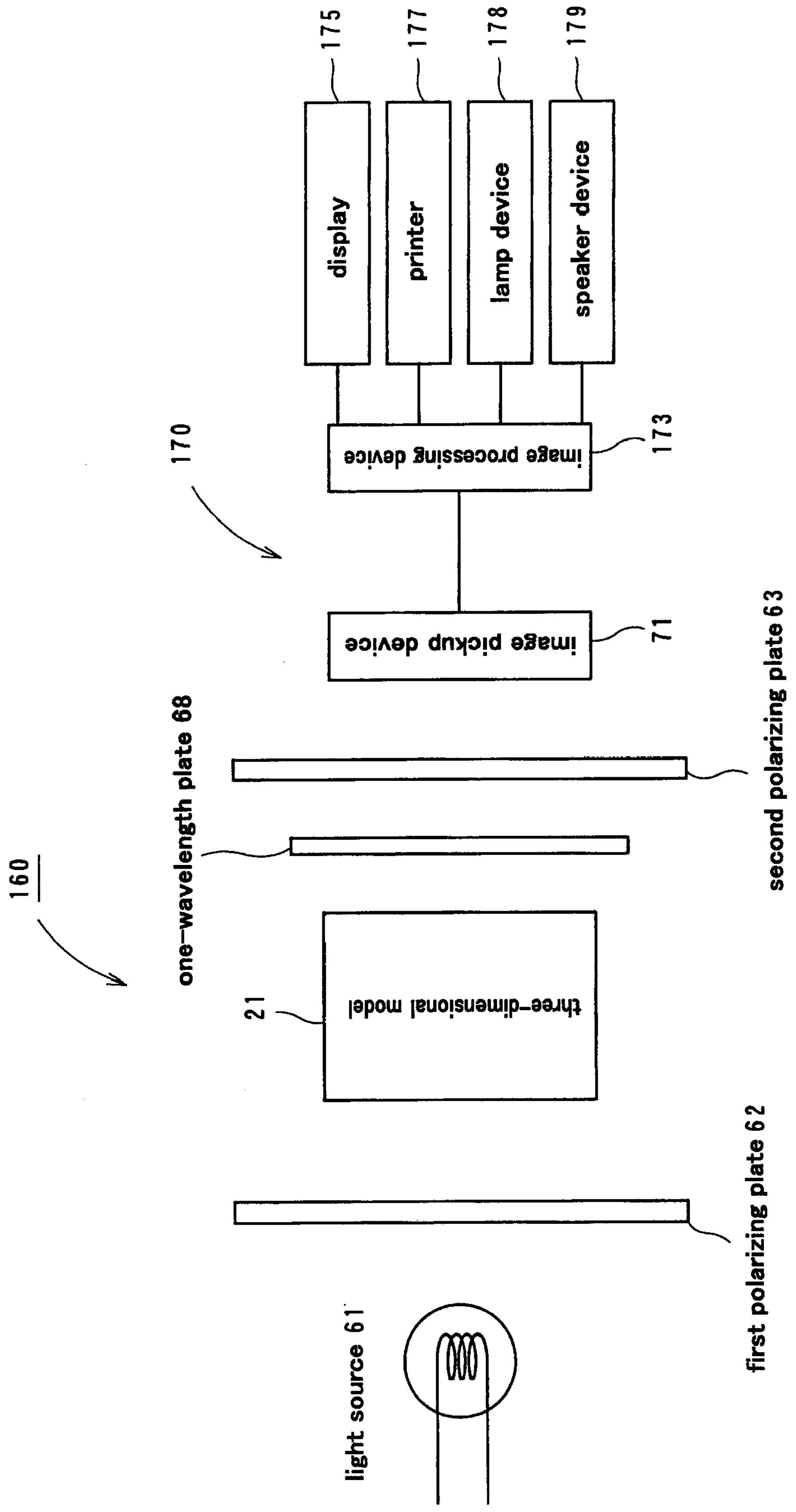
FIG. 13 is a schematic view showing a configuration of a catheter surgery simulator in accordance with another Example of the present invention.

FIG. 13 shows a catheter surgery simulator 160 in accordance with another Example of the present invention. The same reference numerals are given to the same elements in FIG. 9 and description therefor will be omitted herein. In FIG. 13, display 175 and printer 177 constitute an output portion for outputting a state of stress of the membranous model. Lamp device 178 and speaker device 179 constitute an output portion for outputting an alarm. The pair of polarizing plates 62 and 63 and the one-wavelength plate as a phase shift filter form a photoelasticity observation portion.

Figure 14:
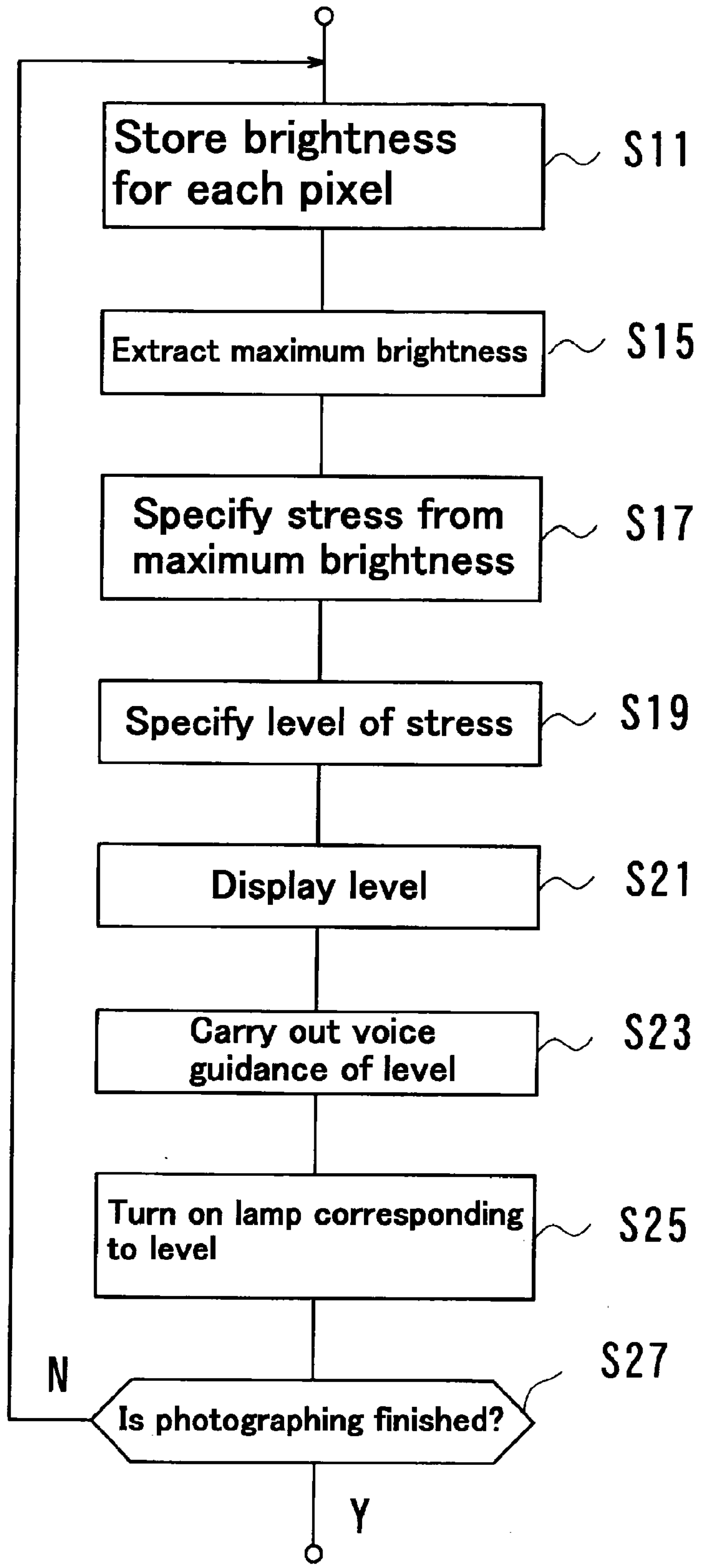
FIG. 14 is a flowchart showing an operation of the catheter surgery simulator.

Next, the operation of the catheter surgery simulator 160 shown in FIG. 13 is described based on a flowchart of FIG. 14.

The portion of the second polarizing plate 63 facing the three-dimensional model 21 is photographed by the image pickup device 71, and the brightness of every pixel, as a feature amount specifying the amount of state of the membranous model, is stored in a predetermined region of a memory of the image processing device (step 11). In step 15, a pixel with the maximum brightness is extracted (step 15), and a stress corresponding to the maximum brightness is specified with reference to the previously prepared table or relation expression (step 17). Then, the level of the stress specified in accordance with a predetermined rule is specified (step 19). For example, the stress can be classified from safety stage, caution stage, and dangerous stage in the order from the smaller stress.

The specified level of the stress can be displayed on the display 175 by numerical values, characters, or bar graph, and other forms (step 21). Needless to say, an image photographed by the image pickup device can be displayed real time on the display 175.

In accordance with the specified level of the stress, the stage can be output as voice guidance via speaker device 179. It is preferable that the voice guidance is carried out when the stage is changed (step 23).

Furthermore, in accordance with the specified level, lamp device 178 can be turned on (step 25). For example, in the safety stage, green lamp is turned on; in the caution stage, yellow lamp is turned on; and when the level becomes in the dangerous stage, red lamp is turned on.

Thus, by outputting an alarm, an operator can concentrate on the insertion of a catheter.

In the above, it is possible to specify the stress from the brightness for each pixel and count the number of pixels beyond the predetermined threshold so as to specify the stress level based on the counted results. Furthermore, it is possible to calculate the stress change for each pixel and to count the number of pixels in which the stress change is beyond the predetermined threshold so as to specify the stress level based on the counted results.

Furthermore, the feature amount may be obtained as follows. The brightness is multiplied by weight coefficient based on the predetermined rule with respect to the pixels in the image photographed by the image pickup device, and the brightness values are added to each other in a predetermined region or an entire region of the image. Thus calculated value is made to be a feature amount.

In the above description, stress is calculated from the brightness. The brightness itself may be used for an arithmetic operation. That is to say, based on the magnitude of the brightness and its rate of change, without carrying out any stress calculation, the level may be determined so as to operate an alarm (voice guidance or lamp).

The stress is specified from the brightness obtained for each pixel, the stress may be multiplied in time sequence. Thus, in the membranous model, the stress stored in the portion corresponding to the pixel (stress history) can be displayed. Furthermore, in accordance with the storage amount (for example, when the storage of stress exceeds the threshold value), the alarm output is allowed to operate.

The reason why the above-mentioned image processing can be carried out is that by intervening the one-wavelength plate, the sensitivity is improved and the image processing can be carried out with high precision.

Figure 15:
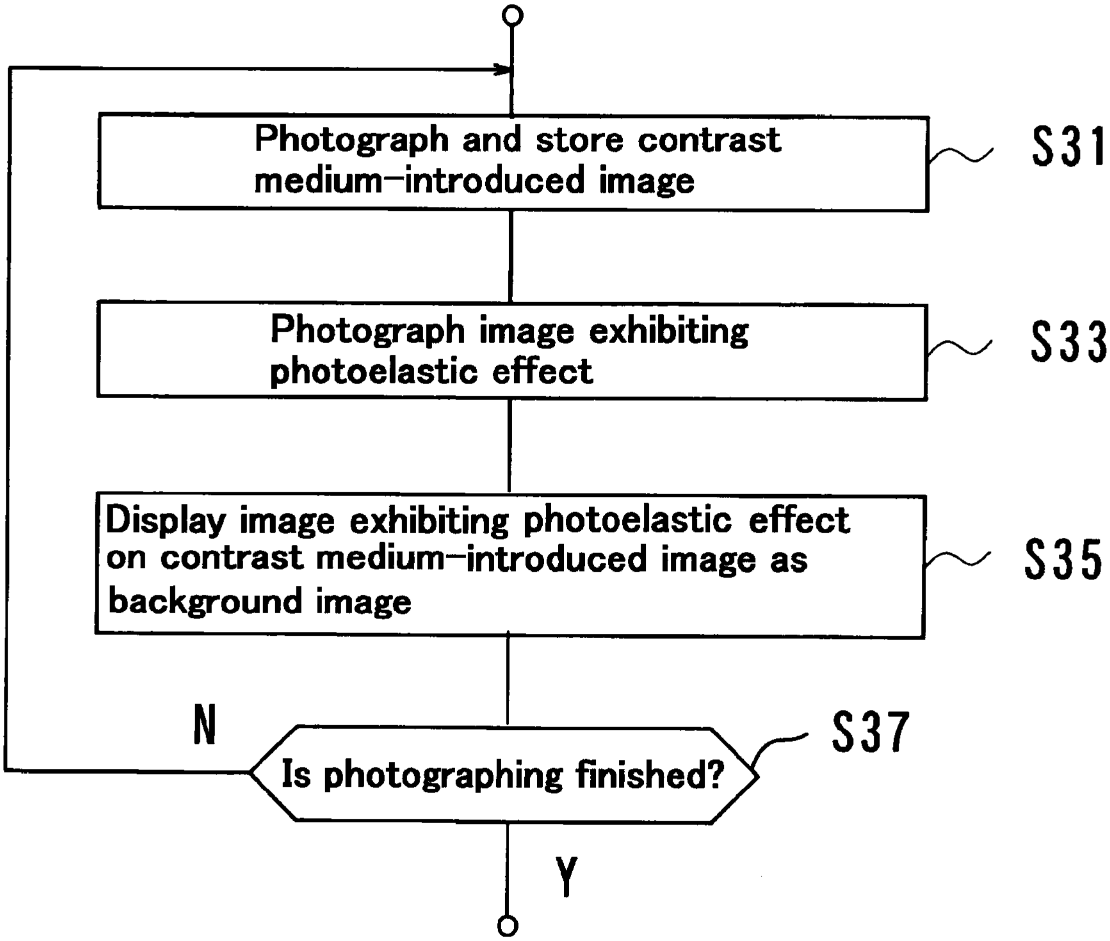
FIG. 15 is a flowchart showing another operation of the catheter surgery simulator.

FIG. 15 shows an Example in which road map formation is simulated in a catheter surgery.

In step 31, a contrast medium is allowed to flow into the blood vessel portion (membranous model portion) of the three-dimensional model 21 and the image of the three-dimensional model 21 is photographed. At this time, by removing at least one of the polarizing plates 62 and 63, preferably removing the polarizing plates 62 and 63 and the one-wavelength plate 68, the light from the light source 61 is allowed to pass through the three-dimensional model 21. The three-dimensional model into which the contrast medium has been introduced is photographed in a state in which the blood vessel portion is colored, and the image is stored (step 31).

Then, in a state shown in FIG. 13, the photoelastic effect of the three-dimensional model, in particular, the membranous model is photographed by the image pickup device 71 (step 33).

The photographed image exhibiting the photoelastic effect is displayed in a state in which it is superimposed on the contrast medium-introduced image as a background image (step 35). Thus, the reliability in the roadmap formation in the catheter surgery can be confirmed.

Figure 16:
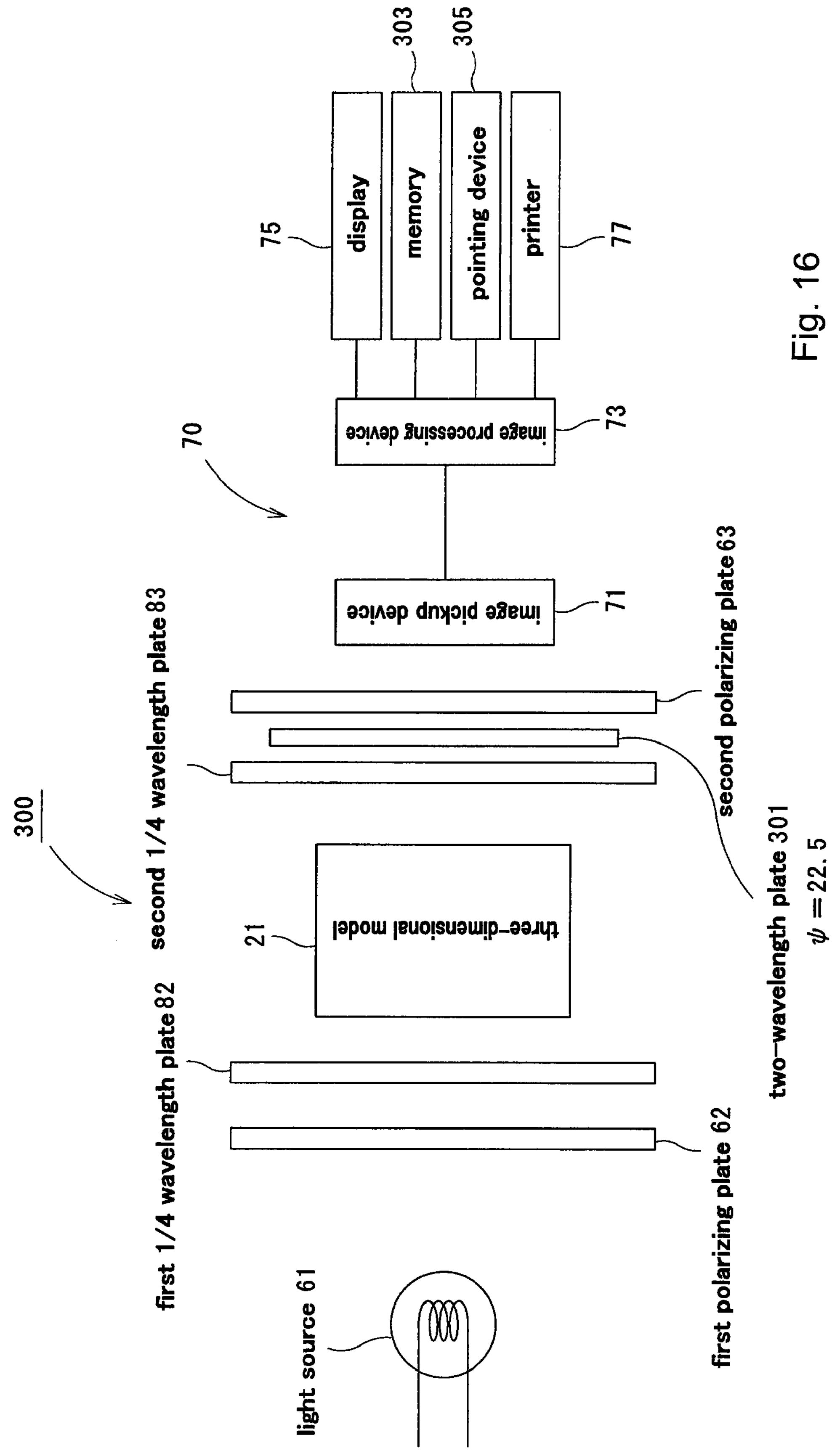
FIG. 16 is a schematic view showing a configuration of the catheter surgery simulator of another Example.

FIG. 16 shows a configuration of a simulator 300 in accordance with another Example. Note here that the same reference numerals are given to the same elements in FIG. 11 and description therefor will be partially omitted herein.

In this Example, a two-wavelength plate 301 is allowed to intervene between a second ¼ wavelength plate 83 and the second polarizing plate 63. This two-wavelength plate is tilted at 22.5° with respect to the optical axis of the ¼ wavelength plate.

Such a configuration corresponds to the configuration shown in FIG. 2. When the color of the light source is allowed to be white, by contrasting the color of light (wavelength) photographed by image pickup device 71 with the color map shown in FIG. 3, the magnitude and direction of the stress applied to the portion in which the photoelastic effect is generated in the three-dimensional model are specified.

In the device 300 of the Example, the color map of FIG. 3 is stored in a memory 303. Furthermore, the arithmetic expression for carrying out an arithmetic operation from the values of retardation (Re) on the abscissa of FIG. 3 is also stored in the memory 303.

Reference numeral 305 denotes a pointing device such as a mouse. In the display 75 for displaying images photographed by the image pickup device 71, it is possible to indicate the desired portion by using a cursor 310 (see FIG. 17).

Figure 17:
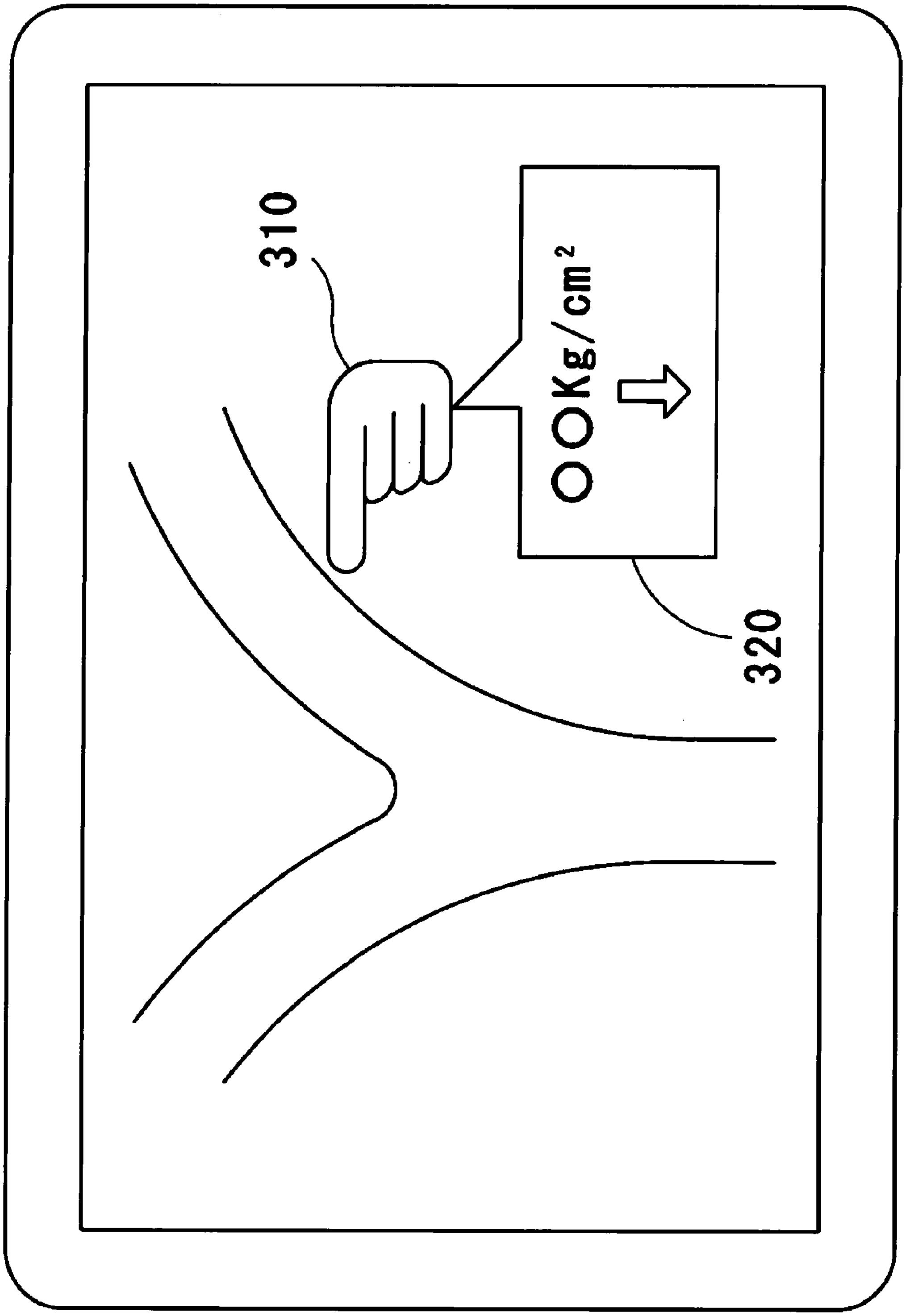
FIG. 17 shows a display mode of a display 75.

The image processing device 73 recognizes the color of the portion indicated by the cursor 310 and the color is contrasted with the color map stored in the memory 303 (see FIG. 3) and the direction and the magnitude of stress are specified. Note here that retardation Re specified in FIG. 3 is substituted in the relation expression stored in the memory 303, the magnitude of stress can be carried out. Then, as shown in FIG. 17, by opening a pop-up window 320, the magnitude of the stress of the portion specified by the cursor 310 is numerically displayed. Furthermore, the direction is shown by an arrow.

Figure 18:
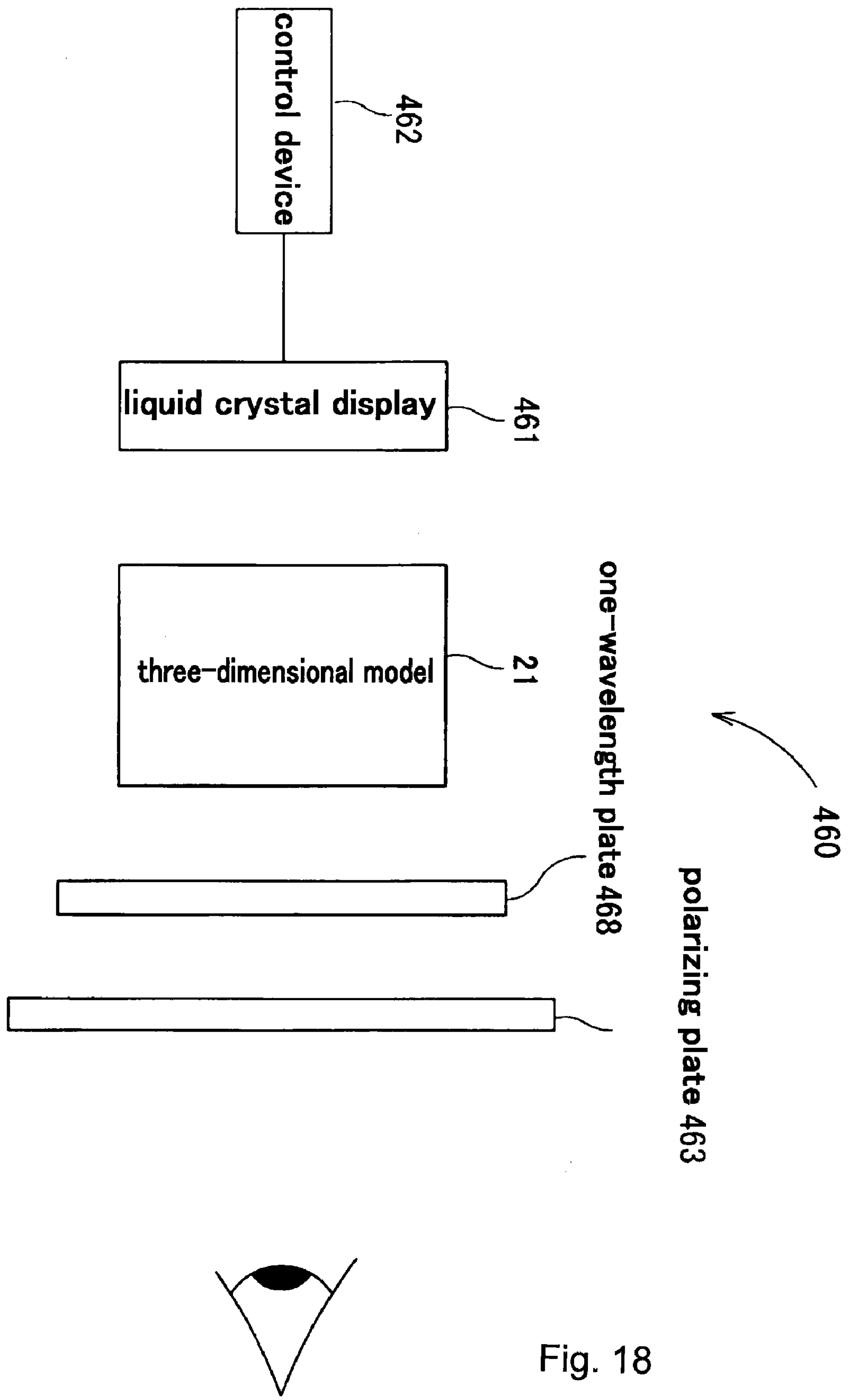
FIG. 18 is a schematic view showing a configuration of the catheter surgery simulator of an Example of the present invention.

FIG. 18 shows a configuration of a catheter surgery simulator 460 in accordance with another Example of the present invention.

The catheter surgery simulator 460 of this Example includes a liquid crystal display 461, a control device thereof 462, a polarizing plate 463 at the observation side, one-wavelength plate 468, and the three-dimensional model 21 shown in FIG. 7.

The liquid crystal display 461 emits polarized light that is right angle with respect to the polarizing plate 463. The control device 462 allows the liquid crystal display to emit light with arbitrary colors. Furthermore, arbitrary images can be displayed on the liquid crystal display 461. The images displayed on the liquid crystal display 461 can be observed via the polarizing plate 463 by the effect of the one-wavelength plate 468.

In this Example, the control device 462 is provided with video image data for guidance and shows an exemplary image of a catheter surgery (a state in which a catheter is inserted into the three-dimensional model). This makes it possible that an operator visually compares the state (seen as a shadow) of the catheter inserted into the three-dimensional model by the operator himself/herself with the exemplary image, thereby improving the training effect.

Figure 19:
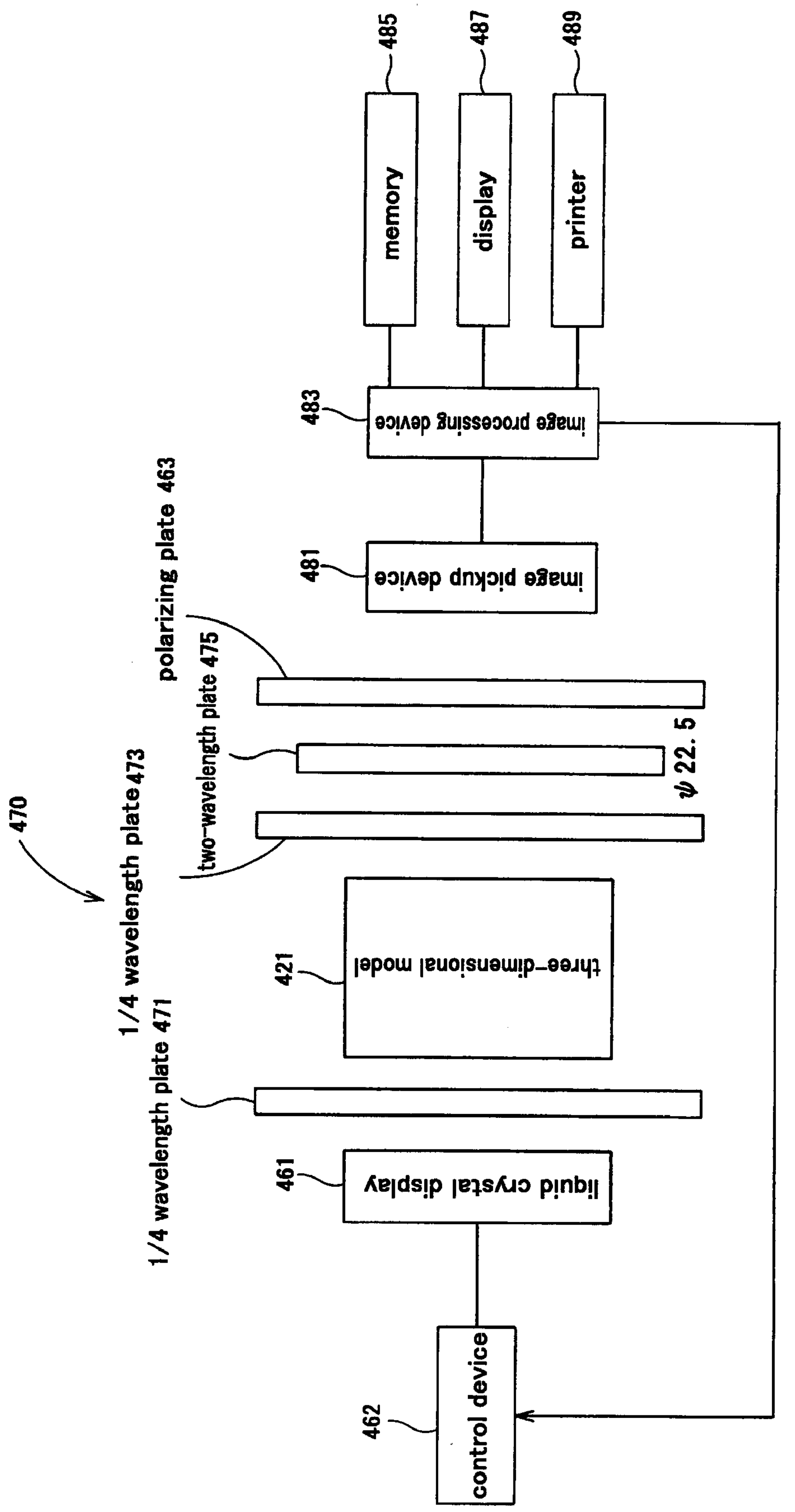
FIG. 19 is a flowchart showing an operation of a photo-receiving portion of a catheter surgery simulator in accordance with another Example.

FIG. 19 shows a configuration of a simulator 470 in accordance with another Example. The same reference numerals are given to the same elements in FIG. 18 and the description therefor will be omitted herein.

In this Example, a two-wavelength plate 475 is employed as a phase shift filter and the two-wavelength plate 475 is disposed between a second ¼ wavelength plate 473 at the observation side and a polarizing plate 463. This two-wavelength plate 475 is tilted at 22.5° with respect to the direction perpendicular to the optical axis. Reference numeral 481 denotes an image pickup device, which includes a CCD array. The image processing device 483 processes the image of photoelastic effect photographed by image pickup device 481. The results of the processing are output to a display 487 or a printer 489. In the memory 485, processing program of the image processing device 483 is stored.

Such a configuration corresponds to the configuration shown in FIG. 2. When the color of the light source is white, by contrasting the color of light (wavelength) photographed by image pickup device 71 with the color map shown in FIG. 3, the magnitude and direction of the stress of the portion in which the photoelastic effect is generated in the three-dimensional model are specified.

The color map shown in FIG. 3 is stored in the memory 485. Furthermore, the arithmetic expression for carrying out an arithmetic operation from the values of retardation (Re) on the abscissa of FIG. 3 is also stored in the memory 485.

The image processing device 483 contrasts the color of the photographed photoelastic effect with the color map stored in the memory 485, and, for example, the magnitude of the stress is specified for each of the predetermined pixels. Then, when the magnitude of the specified stress is beyond the predetermined threshold, the image processing device 483 sends a signal to the control device 462. The control device 462 controls the display mode (image) of the liquid crystal display so that warning is displayed with superimposed on a portion corresponding to the pixels in which the stress is beyond the threshold value. An example of the warning can include displaying a red color strongly, or flashing the portion, or displaying characters and the like on the portion.

In the above-mentioned observation method, in the three-dimensional model, when the portion in which a photoelastic effect is generated has a thickness, the observed photoelastic effect (color of light) is shown as stress superimposed on the portion. Therefore, it is not possible to grasp the distribution of the stress in the inside of the three-dimensional model.

Therefore, this Example has an object to provide a stress detection system capable of specifying the distribution state of the stress inside the three-dimensional model.

In order to achieve the above-mentioned objects, the present inventors have investigated earnestly, they have found that it is possible to specify the distribution of stress in the tomographic surface of the three-dimensional model by applying a X-ray CT scanning technique. That is to say, this Example is configured as follows.

A stress detection system for detecting a photoelastic effect generated in light passing through a translucent three-dimensional model into which a catheter can be inserted, in which a region around a cavity replicating at least a body cavity is formed of an elastic material, which including:

an optical system including a polarized light source, a polarizing filter corresponding to the polarized light source, and an image pickup device for photographing light that has passed through the polarizing filter;

a rotating device for rotating the relative position of the optical system at least 180° around the three-dimensional model disposed between the polarized light source and the polarizing filter; and an arithmetic unit for carrying out an arithmetic operation of the distribution of the strength of stress on the desired tomographic surface of the three-dimensional model by processing a plurality of images photographed in accordance with the rotation.

According to thus configured stress detection system, since the optical system is rotated at least 180° around the three-dimensional model as a center, with respect to the entire region of the three-dimensional model (entire voxel), the light (polarized light) from the light source is allowed to pass through. Thus, in the photoelastic effect (color of light) photographed by an image pickup device at a predetermined rotation angle, a plurality of voxels transmitting the light from the light source are reflected. Therefore, a simultaneous equation holds between the photoelastic effect photographed for each predetermined angle in accordance with the rotation of the optical system and the stress of the voxels through which light passes. By solving the simultaneous equation, the stress of each voxel can be estimated. The stresses of the obtained voxels are aligned corresponding to the desired two-dimensional surface in the three-dimensional model, it is possible to specify the distribution of the stress in a predetermined tomographic surface of the three-dimensional model.

Furthermore, by laminating the two-dimensional stress distribution, three-dimensional stress distribution of the three-dimensional model can be specified.

Figure 20:
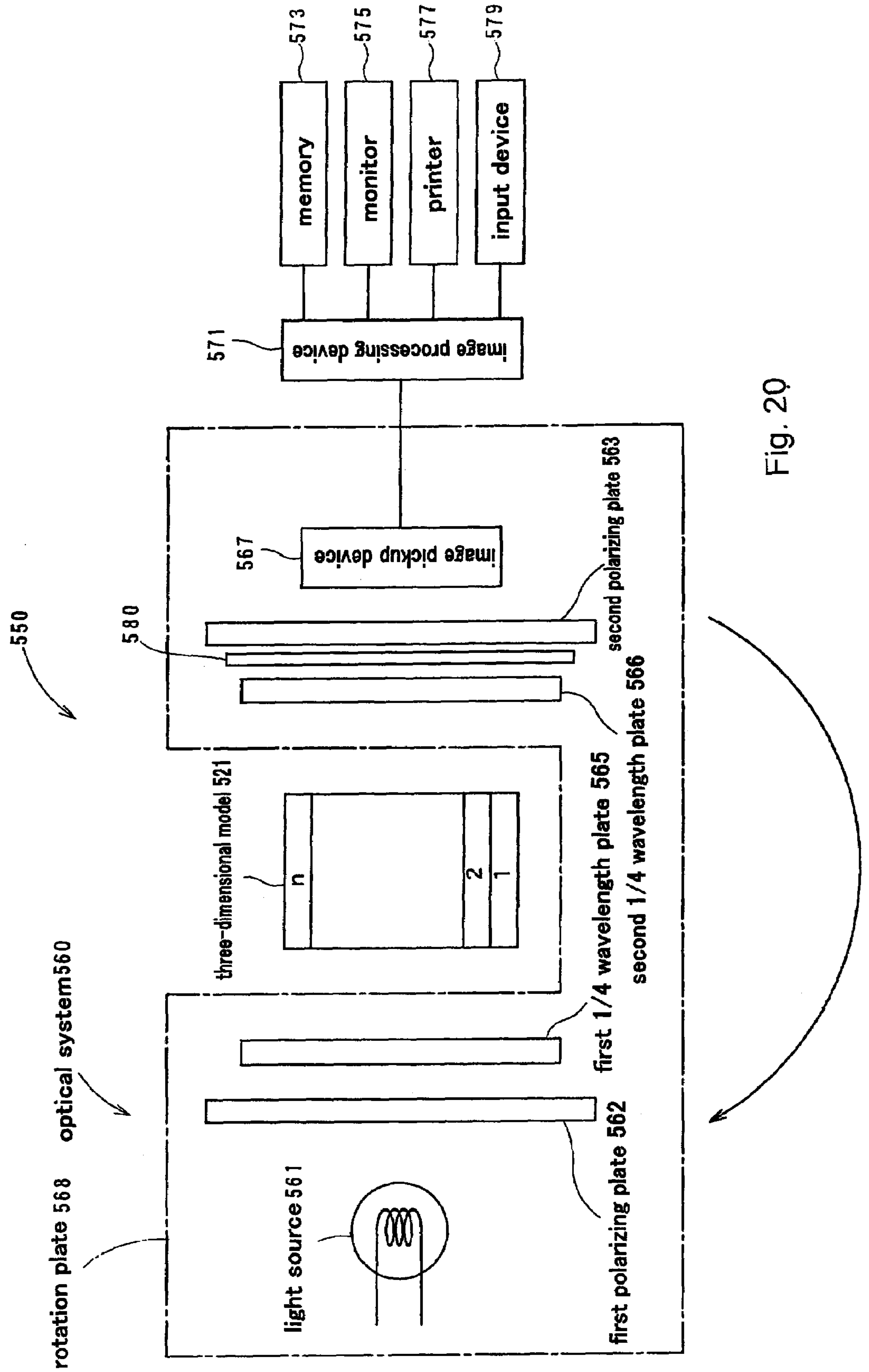
FIG. 20 is a schematic view showing a configuration of a stress observation system in accordance with an Example of the present invention.

FIG. 20 shows a configuration of a stress detection system 550 in accordance with this Example of the present invention.

The stress detection system 550 of this Example includes a three-dimensional model 21, an optical system 560 and an image processing device 571. The optical system 560 includes a light source 561, a pair of polarizing plates 562 and 563, ¼ wavelength plates 565 and 566, as well as an image pickup device 567. Between the second ¼ wavelength plate 566 and the second polarizing plate 563, a one-wavelength plate or a two-wavelength plate is preferably allowed to intervene as a phase shift filter 580. This phase shift filter 580 is tilted at ±5° to ±40° (preferably, ±22.5°) with respect to the optical axis of the ¼ wavelength filter. These elements are fixed to a rotation plate 568. The rotation plate 568 rotates 180° around the three-dimensional model 21 as a center.

The image pickup device 567, in which photo-receiving elements such as CCD and the like are arranged in a plane, is employed. Therefore, the photoelastic effect of the three-dimensional model 21 can be photographed two-dimensionally when photographing is carried out once. Photographing by the image pickup device 567 is carried out for each rotation at a predetermined angle. The photographed two dimensional images are stored in the memory 573.

The image processing device 571 includes a computer device for processing images photographed by the image pickup device 567. Thus, the distribution of the magnitude of the stress inside the three-dimensional model 21 is specified. The specified results are displayed on a monitor 575 or printed in paper by using a printer 577. An input device 579 includes a keyboard or a pointing device for inputting various kinds of parameters and the like necessary to the image processing.

The memory 573 stores a control program for regulating the operation of the computer device of the image processing device 571.

Figure 21:
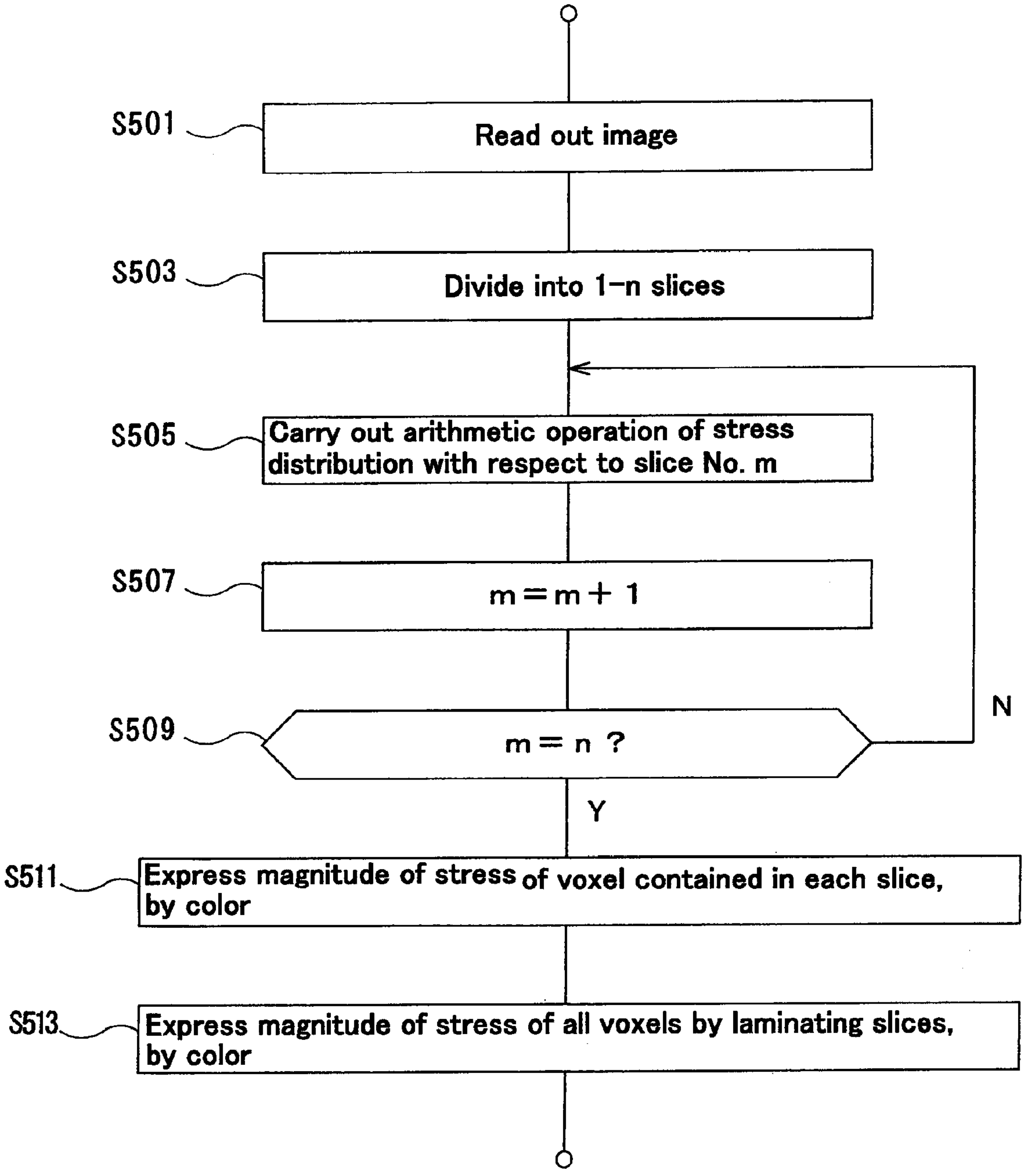
FIG. 21 is a flowchart showing the operation.

The processing of the image processing device 571 is described with reference to the flowchart shown in FIG. 21.

In the step 501, two-dimensional images (images of photographed photoelastic effect) stored in the memory 573 are read out, and divided into one to n slices in the step 503 (step 503). For example, in an example shown in FIG. 20, one to n slices are set in the vertical direction of the paper and from each two dimensional image, a portion corresponding to the slice can be extracted.

In the step 505, a simultaneous equation between voxel (pixel unit) existing in the slice m of the three-dimensional model and the photoelastic effect extracted corresponding to the slice m from each two-dimensional image is set, and a solution of the simultaneous equation is obtained by using a Fourier transformation technique. This solution is a strength of stress of the voxel contained in the slice m.

When the strength of stress of voxel is signified as to all the slices (the steps 507 and 509), a color is given to each voxel in accordance with the strength of stress. For example, to a portion in which the stress is zero, no color (background color) is given. As the stress is increased, red color or green color can be emphasized. Thus, the distribution of stress in each slice is represented by colors (step 511).

In step 513, by laminating slices expressed by color obtained in step 511, the magnitudes of the stress of all the voxels are displayed in colors.

Since the magnitudes of the stress of all the voxels are specified, by arbitrarily extracting the voxel, the slice surface can be changed. For example, in the example shown in FIG. 20, by selecting voxels parallel to the surface, it is possible to obtain the distribution of the strength of stress in the tomogram parallel to the paper.

In the above-mentioned example, the optical system 560 is rotated, however the same effect can be obtained when the three-dimensional model 21 is rotated.

Hereinafter, the following matters are disclosed.

(1) A stress detection system for detecting a photoelastic effect generated in light passing through a translucent three-dimensional model in which at least a region around a cavity replicating the body cavity is formed of an elastic material and into which a catheter can be inserted, including:

an optical system including a polarized light source, a polarizing filter corresponding to the polarized light source, and an image pick-up device for photographing light that has passes through the polarizing filter;

a rotating device for rotating the relative position of the optical system at least 180° around the three-dimensional model disposed between the polarized light source and the polarizing filter; and an arithmetic unit for processing a plurality of images photographed in accordance with the rotation and carrying out an arithmetic operation of the distribution of stress in a desired tomographic surface of the three-dimensional model.

(2) The stress detection system described in (1), further including a second arithmetic unit for carrying out an arithmetic operation of the distribution of the three dimensional stress of the three-dimensional model by laminating the distribution of the strength of stress in the tomographic surface.

(3) The stress detection system described in (1) or (2) further comprising an output device for outputting the distribution of the stress.

The present invention is not limited to the description of the above exemplary embodiments and Examples. A variety of modifications, which are within the scopes of the following claims and which are easily achieved by a person skilled in the art, are included in the present invention.

The invention claimed is:

1. A catheter surgery simulator, which is a stress observation system of a three-dimensional model for detecting a photoelastic effect generated in light passing through a translucent three-dimensional model in which at least a region around a cavity replicating the body cavity is formed of an elastic material and into which a catheter can be inserted, comprising:

a polarized light source and its corresponding polarizing filter at an observation side; and a phase shift filter disposed at an inner side of the polarized light source and its corresponding polarizing filter at the observation side, which allows a part of the light from the light source as a background color to pass through the polarizing filter at the observation side;

wherein both of the photo elastic effect and a shadow of a catheter inserted in the three-dimensional model are made to be visible.

2. The catheter surgery simulator according to claim 1, wherein the phase shift filter includes a one-wavelength plate or a two-wavelength plate.

3. The catheter surgery simulator according to claim 1, wherein a pair of ¼ wavelength filters are disposed for realizing a circular polarizing observation at the inner side of the polarized light source and the polarizing filter at the observation side, the phase shift filter is disposed between the polarizing filter at the observation side and the ¼ wavelength filter that is closer to the polarizing filter, or between the polarized light source and the ¼ wavelength filter that is closer to the light source, and the phase shift filter is tilted at ±5° to ±40 ° with respect to an optical axis of the ¼wavelength filter.

4. The catheter surgery simulator according to claim 3, wherein the phase shift filter is tilted at ±22.5° with respect to an optical axis of the ¼ wavelength filter.

5. The catheter surgery simulator according to claim 1, wherein a pair of ¼ wavelength filters are disposed for realizing a circular polarizing observation at the inner side of the polarized light source and the polarizing filter at the observation side, and the phase shift filter is disposed between the pair of ¼ wavelength filters.

6. The catheter surgery simulator according to claim 1, wherein the polarizing filter at the observation side and the phase shift filter are laminated so as to form a window portion of glasses.

7. The catheter surgery simulator according to claim 1, wherein the membranous model is surrounded by a base material made of gel that hardly generates a photoelastic effect as compared with the membranous model and that is adhesive with respect to the membranous model.

8. The catheter surgery simulator according to claim 7, further comprising a casing that is translucent and contains the base material, wherein the base material has a margin permitting free deformation of the membranous model between the casing and the membranous model.

9. The catheter surgery simulator according to claim 7, wherein the membranous model includes urethane resin or urethane elastomer and the base material includes a silicone gel.

10. The catheter surgery simulator according to claim 1, wherein the polarized light source includes a white light source and a polarizing filter.

11. The catheter surgery simulator according to claim 4, wherein green color light is emitted from the polarized light source.

12. The catheter surgery simulator according to claim 1, wherein the polarized light source includes a display device.

13. The catheter surgery simulator according to claim 12, wherein the display device includes a liquid crystal display for emitting a polarized light.

14. The catheter surgery simulator according to claim 12, further comprising an image pickup portion for photographing the photoelastic effect, and a predetermined display is carried out on the display device based on the photographed results by the image pickup portion.

15. A stress observation method of a three-dimensional model, comprising;

inserting a catheter into a translucent three-dimensional model in which at least a region around a cavity replicating the body cavity is formed of an elastic material, disposing the three-dimensional model between a polarized light source and its corresponding polarizing filter, thereby generating a photoelastic effect corresponding to the stress generated by the catheter in the region around thereof; and allowing a phase shift filter to intervene between the polarized light source and its corresponding polarizing filter, thereby allowing a shadow of the catheter inserted in the three-dimensional model to be observed together with the photoelastic effect.

16. A stress observing method of a three-dimensional model, comprising:

inserting a catheter into a translucent three-dimensional model in which at least a region around a cavity replicating the body cavity is formed of an elastic material;

disposing the three-dimensional model between a polarized light source and its corresponding polarizing filter, thereby generating a photoelastic effect corresponding to the stress generated by the catheter in the region around thereof; and disposing the polarizing filter in a state in which it is not orthogonal to the polarized light source, thereby allowing a shadow of the catheter inserted in the three-dimensional model to be observed together with the photoelastic effect.

17. The catheter surgery simulator according to claim 1, further comprising an image pickup portion for photographing a photoelastic effect of the three-dimensional model;

an image processing portion for processing images photographed by the image pickup portion and generating a feature amount for specifying a state of the three-dimensional model; and an output portion for outputting a feature amount generated in the image processing portion or outputting an alarm based on the feature amount.

18. The catheter surgery simulator according to claim 17, wherein the feature amount is a stress value.

19. The catheter surgery simulator according to claim 17, wherein the feature amount is a calculated value obtained by adding brightness of pixels or the brightness of the pixels multiplied by weight coefficient based on a predetermined rule in the pixels in a certain region.

20. The catheter surgery simulator according to claim 17, further comprising a means of multiplying the feature amount specified in the image processing portion.

21. The catheter surgery simulator according to claim 17, further comprising a means for storing images in a state in which a contrast medium is introduced into the membranous model, wherein the output portion displays a photoelastic effect photographed by the image pickup portion, which is superimposed on the image.

22. The catheter surgery simulator according to claim 1, further comprising a means for specifying a direction of stress and/or a magnitude of stress based on the detected photoelastic effect.

23. The catheter surgery simulator according to claim 3, further comprising an image pickup device for photographing light that has passed through the polarizing filter at the observation side;

a rotating device for rotating the relative position of the optical system at least 180° around the three-dimensional model disposed between the polarized light source and the polarizing filter; and an arithmetic unit for processing a plurality of images photographed in accordance with the rotation and carrying out an arithmetic operation of a distribution of the stress in a desired tomographic surface of the three-dimensional model.

24. The catheter surgery simulator according to claim 23, further comprising a second arithmetic unit for carrying out an arithmetic operation of a distribution of the three-dimensional stress of the three-dimensional model by laminating the distribution of the strength of stress in the tomographic surface.

25. The catheter surgery simulator according to claim 23, further comprising an output device for outputting the distribution of the stress.

* * * * *